(12) United States Patent
Kong et al.

(10) Patent No.: US 11,883,661 B2
(45) Date of Patent: Jan. 30, 2024

(54) INTELLIGENT DETERMINATION OF THERAPEUTIC STIMULATION INTENSITY FOR TRANSCUTANEOUS ELECTRICAL NERVE STIMULATION

(71) Applicant: Neurometrix, Inc., Woburn, MA (US)

(72) Inventors: Xuan Kong, Acton, MA (US); Rebecca A. Burrell, Rowley, MA (US); Shai N. Gozani, Newton, MA (US)

(73) Assignee: Neurometrix, Inc., Woburn, MA (US)

( * ) Notice: Subject to any disclaimer, the term of this patent is extended or adjusted under 35 U.S.C. 154(b) by 336 days.

(21) Appl. No.: 16/705,960

(22) Filed: Dec. 6, 2019

(65) Prior Publication Data

US 2020/0179694 A1 Jun. 11, 2020

Related U.S. Application Data

(60) Provisional application No. 62/892,627, filed on Aug. 28, 2019, provisional application No. 62/776,834, filed on Dec. 7, 2018.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/36021* (2013.01)

(58) Field of Classification Search
CPC ............ A61N 1/36132; A61N 1/36021; A61N 1/36034; A61N 1/0456
See application file for complete search history.

(56) References Cited

U.S. PATENT DOCUMENTS 1,741,962 A 12/1929 Theodoropulos
4,290,431 A 9/1981 Herbert et al.
(Continued)

FOREIGN PATENT DOCUMENTS

CN 1665563 9/2005
CN 1919139 2/2007
(Continued)

OTHER PUBLICATIONS

Desantana, J.M. et al., Effectiveness of transcutaneous electrical nerve stimulation for treatment of hyperalgesia and pain, Curr Rheumatol Rep., 2008, vol. 10. No. 6, pp. 492-499.
(Continued)

*Primary Examiner* — Alyssa M Alter
(74) *Attorney, Agent, or Firm* — Pandiscio & Pandiscio

(57) ABSTRACT

Apparatus for assessing the accuracy of a target stimulation intensity level used in transcutaneous electrical nerve stimulation to a user, the apparatus comprising: a calculation unit for calculating a set of expected values of the target stimulation intensity level for a desired sensation based on a profile of the user; a stimulation unit for electrically stimulating at least one nerve of the user at one or more stimulation levels; a discovery unit for enabling the user to indicate a target stimulation intensity level at which the electrical stimulation to the user evokes the desired sensation from the user; and an assessment unit to determine the accuracy of the indicated target stimulation intensity level based on the expected set of values of the target stimulation intensity level for the desired sensation.

18 Claims, 14 Drawing Sheets

(56) References Cited

U.S. PATENT DOCUMENTS

| | | |
|---|---|---|
| D263,869 S | 4/1982 | Sumiyasu |
| 4,503,863 A | 3/1985 | Katims |
| 4,605,010 A | 8/1986 | McEwen |
| 4,738,250 A | 4/1988 | Fulkerson et al. |
| 4,777,711 A | 10/1988 | Forkner et al. |
| 4,926,863 A | 5/1990 | Alt |
| 4,989,605 A | 2/1991 | Rossen |
| 5,048,523 A | 9/1991 | Yamasawa et al. |
| 5,063,929 A | 11/1991 | Bartelt et al. |
| D323,561 S | 1/1992 | Bartelt et al. |
| 5,121,747 A | 6/1992 | Andrews |
| 5,169,384 A | 12/1992 | Bosniak et al. |
| D342,571 S | 12/1993 | Givens, Sr. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,948,000 A | 9/1999 | Larsen et al. |
| 5,954,758 A | 9/1999 | Peckham et al. |
| 6,033,370 A | 3/2000 | Reinbold et al. |
| 6,099,488 A | 8/2000 | Hung |
| 6,132,387 A | 10/2000 | Gozani et al. |
| 6,141,587 A | 10/2000 | Mower |
| 6,148,233 A | 11/2000 | Owen et al. |
| 6,161,044 A | 12/2000 | Silverstone |
| D443,362 S | 6/2001 | Storp |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,611,789 B1 | 8/2003 | Darley |
| 6,662,051 B1 | 12/2003 | Eraker et al. |
| D484,984 S | 1/2004 | Takizawa et al. |
| D534,871 S | 1/2007 | Larsen |
| D541,042 S | 4/2007 | Andre et al. |
| D547,454 S | 7/2007 | Hsieh |
| D566,383 S | 4/2008 | Harris et al. |
| D584,414 S | 1/2009 | Lash et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,016 S | 10/2010 | Potts et al. |
| D625,829 S | 10/2010 | Arbesman et al. |
| D629,115 S | 12/2010 | Robertson |
| 7,887,493 B2 | 2/2011 | Stahmann et al. |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| 8,284,070 B2 | 10/2012 | Chaudhari et al. |
| D677,792 S | 3/2013 | Vandiver |
| D680,735 S | 4/2013 | Itabashi et al. |
| 8,421,642 B1 | 4/2013 | McIntosh et al. |
| D687,951 S | 8/2013 | Della Torre et al. |
| D688,707 S | 8/2013 | Vincent et al. |
| D704,848 S | 5/2014 | Thomas et al. |
| D705,428 S | 5/2014 | Cheney et al. |
| D712,045 S | 8/2014 | Thornton |
| D712,052 S | 8/2014 | Thomas et al. |
| D713,049 S | 9/2014 | Shah |
| 8,825,175 B2 | 9/2014 | King |
| 8,849,407 B1 | 9/2014 | Danilov et al. |
| D716,457 S | 10/2014 | Brefka et al. |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| D735,873 S | 8/2015 | Brefka et al. |
| 9,168,375 B2 | 10/2015 | Rahimi et al. |
| D744,661 S | 12/2015 | Rizzi |
| D745,975 S | 12/2015 | Igaue et al. |
| D750,263 S | 2/2016 | Shigeno et al. |
| D750,798 S | 3/2016 | Yosef et al. |
| 9,282,287 B1 | 3/2016 | Marsh |
| 9,282,897 B2 | 3/2016 | Ross, Jr. et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D775,361 S | 12/2016 | Vosch et al. |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| 9,700,724 B2 | 7/2017 | Liu et al. |
| D794,331 S | 8/2017 | Grote |
| 9,731,126 B2 | 8/2017 | Ferree et al. |
| D798,170 S | 9/2017 | Toth et al. |
| D801,542 S | 10/2017 | Anderson |
| D802,780 S | 11/2017 | Hsu |
| 9,827,420 B2 | 11/2017 | Ferree et al. |
| D806,669 S | 1/2018 | Kangasmaa et al. |
| D810,311 S | 2/2018 | Chen |
| D810,843 S | 2/2018 | Karvandi |
| D810,952 S | 2/2018 | Hsu |
| D811,729 S | 3/2018 | Bysshe |
| D813,405 S | 3/2018 | Ho |
| D813,407 S | 3/2018 | Chen |
| D813,408 S | 3/2018 | Chen |
| D821,592 S | 6/2018 | Pham et al. |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| 10,154,922 B1 | 12/2018 | Perez et al. |
| D837,394 S | 1/2019 | Cryan et al. |
| 10,279,179 B2 | 5/2019 | Gozani |
| 10,335,595 B2 | 7/2019 | Ferree et al. |
| D857,910 S | 8/2019 | Cryan et al. |
| D861,903 S | 10/2019 | Cryan et al. |
| D861,904 S | 10/2019 | Ho |
| D862,716 S | 10/2019 | Cryan et al. |
| D865,986 S | 11/2019 | Cryan et al. |
| D879,983 S | 3/2020 | Wang |
| 10,940,311 B2 | 3/2021 | Gozani et al. |

(56) References Cited

U.S. PATENT DOCUMENTS

| | | |
|---|---|---|
| 11,247,040 B2 | 2/2022 | Ferree et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0049241 A1 | 3/2004 | Campos |
| 2004/0122483 A1 | 6/2004 | Nathan et al. |
| 2004/0173220 A1 | 9/2004 | Harry et al. |
| 2005/0059903 A1 | 3/2005 | Izumi |
| 2005/0080463 A1 | 4/2005 | Stahmann et al. |
| 2005/0097970 A1 | 5/2005 | Nurse |
| 2005/0131317 A1 | 6/2005 | Oddsson et al. |
| 2005/0234525 A1 | 10/2005 | Phillips |
| 2005/0283204 A1 | 12/2005 | Buhlmann et al. |
| 2006/0052788 A1 | 3/2006 | Thelen et al. |
| 2006/0064037 A1 | 3/2006 | Shalon et al. |
| 2006/0085047 A1 | 4/2006 | Unsworth et al. |
| 2006/0085049 A1 | 4/2006 | Cory et al. |
| 2006/0089683 A1 | 4/2006 | Hagglof et al. |
| 2006/0095088 A1 | 5/2006 | De Ridder |
| 2006/0173507 A1 | 8/2006 | Mrva et al. |
| 2006/0190057 A1 | 8/2006 | Reese |
| 2006/0251334 A1 | 11/2006 | Oba et al. |
| 2007/0021786 A1 | 1/2007 | Pamis et al. |
| 2007/0060922 A1 | 3/2007 | Dreyfuss |
| 2007/0203435 A1 | 8/2007 | Novak |
| 2007/0203547 A1 | 8/2007 | Costello et al. |
| 2007/0276449 A1 | 11/2007 | Gunter et al. |
| 2008/0009772 A1 | 1/2008 | Tyler et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0172102 A1 | 7/2008 | Shalev |
| 2008/0312709 A1 | 12/2008 | Volpe et al. |
| 2009/0030476 A1 | 1/2009 | Hargrove |
| 2009/0076364 A1 | 3/2009 | Libbus et al. |
| 2009/0082829 A1 | 3/2009 | Panken et al. |
| 2009/0082831 A1 | 3/2009 | Paul et al. |
| 2009/0112214 A1 | 4/2009 | Philippon et al. |
| 2009/0131993 A1 | 5/2009 | Rousso et al. |
| 2009/0203972 A1 | 8/2009 | Heneghan et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0010585 A1 | 1/2010 | Davis et al. |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2010/0274304 A1 | 10/2010 | Wang et al. |
| 2011/0066209 A1 | 3/2011 | Bodlaender et al. |
| 2011/0106213 A1 | 5/2011 | Davis et al. |
| 2011/0166622 A1 | 7/2011 | Crosson et al. |
| 2011/0190594 A1 | 8/2011 | Heit et al. |
| 2011/0224665 A1 | 9/2011 | Crosby et al. |
| 2011/0245711 A1 | 10/2011 | Katra et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2012/0123227 A1 | 5/2012 | Sun et al. |
| 2012/0130449 A1 | 5/2012 | Carlyon et al. |
| 2012/0303077 A1 | 11/2012 | De Vincentiis |
| 2012/0319816 A1 | 12/2012 | Al-Ali |
| 2013/0079846 A1 | 3/2013 | Single |
| 2013/0096641 A1 | 4/2013 | Strother et al. |
| 2013/0116514 A1 | 5/2013 | Kroner et al. |
| 2013/0158627 A1 | 6/2013 | Gozani et al. |
| 2013/0197341 A1 | 8/2013 | Grob et al. |
| 2013/0217998 A1 | 8/2013 | Mahfouz et al. |
| 2013/0317333 A1 | 11/2013 | Yang et al. |
| 2014/0005759 A1 | 1/2014 | Fahey et al. |
| 2014/0039450 A1 | 2/2014 | Green et al. |
| 2014/0057232 A1 | 2/2014 | Wetmore et al. |
| 2014/0081353 A1 | 3/2014 | Cook et al. |
| 2014/0088192 A1 | 3/2014 | Heller et al. |
| 2014/0107729 A1 | 4/2014 | Sumners et al. |
| 2014/0163444 A1 | 6/2014 | Ingvarsson et al. |
| 2014/0188194 A1 | 7/2014 | Schepis et al. |
| 2014/0206976 A1 | 7/2014 | Thompson et al. |
| 2014/0221797 A1 | 8/2014 | Bailey et al. |
| 2014/0245784 A1 | 9/2014 | Proud et al. |
| 2014/0245791 A1 | 9/2014 | Proud et al. |
| 2014/0276236 A1 | 9/2014 | Swain et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336725 A1 | 11/2014 | Nogueira |
| 2014/0336730 A1 | 11/2014 | Simon et al. |
| 2014/0343625 A1 | 11/2014 | Laighin |
| 2014/0371547 A1 | 12/2014 | Gartenberg et al. |
| 2014/0371814 A1 | 12/2014 | Spizzirri et al. |
| 2014/0379045 A1 | 12/2014 | Rahimi et al. |
| 2015/0012068 A1 | 1/2015 | Bradley et al. |
| 2015/0045853 A1 | 2/2015 | Alataris et al. |
| 2015/0100107 A1 | 4/2015 | Kiani et al. |
| 2015/0157242 A1 | 6/2015 | Sabesan |
| 2015/0157868 A1 | 6/2015 | Franke et al. |
| 2015/0174402 A1 | 6/2015 | Thomas et al. |
| 2015/0238094 A1 | 8/2015 | Lai et al. |
| 2015/0272511 A1 | 10/2015 | Najafi et al. |
| 2015/0306387 A1 | 10/2015 | Kong et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2015/0335877 A1 | 11/2015 | Jeffery et al. |
| 2016/0007931 A1 | 1/2016 | Rubin et al. |
| 2016/0029891 A1 | 2/2016 | Lin |
| 2016/0113551 A1 | 4/2016 | Annegarn et al. |
| 2016/0144174 A1 | 5/2016 | Ferree et al. |
| 2016/0151628 A1 | 6/2016 | Simon et al. |
| 2016/0166198 A1 | 6/2016 | Oddsson et al. |
| 2016/0189371 A1 | 6/2016 | Krishna Rao et al. |
| 2016/0213924 A1 | 7/2016 | Coleman et al. |
| 2016/0235981 A1 | 8/2016 | Southwell et al. |
| 2016/0242646 A1 | 8/2016 | Obma |
| 2016/0243359 A1* | 8/2016 | Sharma .................. A61F 7/007 |
| 2016/0250464 A1 | 9/2016 | Zschaeck et al. |
| 2016/0310730 A1 | 10/2016 | Martins et al. |
| 2016/0367823 A1 | 12/2016 | Cowan et al. |
| 2017/0043160 A1 | 2/2017 | Goodall et al. |
| 2017/0056650 A1 | 3/2017 | Cohen et al. |
| 2017/0188864 A1 | 7/2017 | Drury |
| 2017/0188872 A1 | 7/2017 | Hughes et al. |
| 2017/0209693 A1 | 7/2017 | An et al. |
| 2017/0224990 A1 | 8/2017 | Goldwasser et al. |
| 2017/0238812 A1 | 8/2017 | Atlas |
| 2017/0368345 A1 | 12/2017 | Kong et al. |
| 2018/0000685 A1 | 1/2018 | Maloney et al. |
| 2018/0028808 A1 | 2/2018 | Ferree et al. |
| 2018/0132757 A1 | 5/2018 | Kong et al. |
| 2018/0177996 A1 | 6/2018 | Gozani et al. |
| 2018/0345014 A1 | 12/2018 | Gozani et al. |
| 2019/0001135 A1 | 1/2019 | Yoo et al. |
| 2019/0022372 A1 | 1/2019 | Dar et al. |
| 2019/0022386 A1 | 1/2019 | Gozani et al. |
| 2019/0134393 A1 | 5/2019 | Wong et al. |
| 2020/0179694 A1 | 6/2020 | Kong et al. |
| 2020/0219615 A1 | 7/2020 | Rabin et al. |

(56) References Cited

U.S. PATENT DOCUMENTS

| | | |
|---|---|---|
| 2021/0128904 A1 | 5/2021 | Terekhov |
| 2021/0260374 A1 | 8/2021 | Gozani et al. |

FOREIGN PATENT DOCUMENTS

| | | |
|---|---|---|
| CN | 1926496 | 3/2007 |
| CN | 101557788 | 10/2009 |
| CN | 101626804 | 1/2010 |
| CN | 102202131 | 9/2011 |
| CN | 102355847 | 2/2012 |
| CN | 102740919 | 10/2012 |
| DE | 102010052710 | 5/2012 |
| EP | 0971653 | 1/2000 |
| EP | 1 985 277 | 2/2015 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2013/028960 | 2/2013 |
| WO | WO 2014/172381 | 10/2014 |
| WO | WO 2015/123373 | 8/2015 |
| WO | WO 2016/201366 | 12/2016 |
| WO | WO 2018/089655 | 5/2018 |
| WO | WO 2020/033883 | 2/2020 |

OTHER PUBLICATIONS

Melzack, R. et al., Pain Mechanisms: A New Theory, Science, Nov. 19, 1965, vol. 150, No. 3699, pp. 971-979.

Moran, F. et al., Hypoalgesia in Response to Transcutaneous Electrical Nerve Stimulation (TENS) Depends on Stimulation Intensity, J Pain, Aug. 2011, vol. 12, No. 8, pp. 929-935.

Waeber, R. et al., Biosection Search with Noisy Responses, SIAM J. Control Optim., 2013, vol. 51, No. 3, pp. 2261-2279.

Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.

Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.

Ossipov MH et al., Central Modulation of Pain, The Journal of Clinical Investigation, Nov. 2010, vol. 120, No. 11, pp. 3779-3787.

Taborri et al., A Novel HMM Distributed Classifier for the Detection of Gait Phases by Means of a Wearable Inertial Sensor Network, Sensors, Sep. 2014, vol. 14, pp. 16212-16234.

Vance et al., Using TENS for pain control: the state of the evidence, Pain Management, 2014, vol. 4, No. 3, pp. 197-209.

Amazon, "Quell 2.0 Wearable Pain Relief Technology", Sep. 15, 2018.http://www.amazon/com/Quell-Wearable-Pain-Relief-Technology/dp/B07DHW2MJJ/ref=cm_cr_arp_d_product_top? ie=UTF8. Shown on p. 1. (Year: 2018).

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Amft, O. et al., Sensing Muscle Activities with Body-Worn Sensors, Conference Paper, May 2006.

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bifulco, P. et al., A Stretchable Conductive Rubber Sensor to Detect Muscle Contraction for Prosthetic Hand Control, The 6th IEEE International Conference on E-Health and Bioengineering—EHB 2017, Jun. 22-24, 2017, pp. 173-176.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.

Davies HTO et al., Diminishing returns or appropriate treatment strategy?—an analysis of short-term outcomes after pain clinic treatment, Pain, 1997, vol. 70: 203-208.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

(56) References Cited

OTHER PUBLICATIONS

Fary RE et al., Monophasic electrical stimulation produces high rates of adverse skin reactions in healthy subjects, Physiotherapy Theory and Practice, 2011, vol. 27(3): 246-251.
Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6):639-647.
Fishbain, David A. et al., Transcutaneous Electrical Nerve Stimulation (TENS) Treatment Outcome in Long-Term Users, The Clinical Journal of Pain, Sep. 1996; 12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Hausdorff, J.M. et al., Gait Variability and Fall Risk in Community-Living Older Adults: A 1-Year Prospective Study, Arch Phys Med Rehabil, Aug. 2001, vol. 82, pp. 1050-1056.
Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels and Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement. J. Comp. Physiol. Psychol. Oct. 1959; 52:629-634.
Lykken, D.T., Square-Wave Analysis of Skin Impedance. Psychophysiology. Sep. 1970; 7(2):262-275.
MacFarlane, T. et al., Whether the weather influences pain? Results from EpiFunD study in North West England, Rheumatology, 2010, vol. 49, pp. 1513-1520.
Nightingale, S., The neuropathic pain market, Nature Reviews, 2012, vol. 11, p. 101-102.
Okamoto-Mizuno. K. et al., Effects of thermal environment on sleep and circadlan rhythm, Journal of Physiological Anthropology, 2012, vol. 31, No. 14, pp. 1-9.
Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.
Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.
Sano, A et al, Quantitative analysis of wrist electrodermal activity during sleep, International Journal of Psychophysiology, 2014, vol. 94, pp. 382-389.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Sheridan et al., Some Factors Influencing the Threshold of the Electrocutaneous Stimulus, Perceptual and Motor Skills, 1966, vol. 22, pp. 647-654.
Susi et al., Motion Mode Recognition and Step Detection Algorithms for Mobile Phone Users, Sensors, Jan. 24, 2013, vol. 13, pp. 1539-1562.
Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.
Tryon, W. W., Issues of Validity in Actigraphic Sleep Assessment, Sleep, 2004, 27(1), p. 158-165.
Tsai, Y et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977; 15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

(56) References Cited

OTHER PUBLICATIONS

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

* cited by examiner

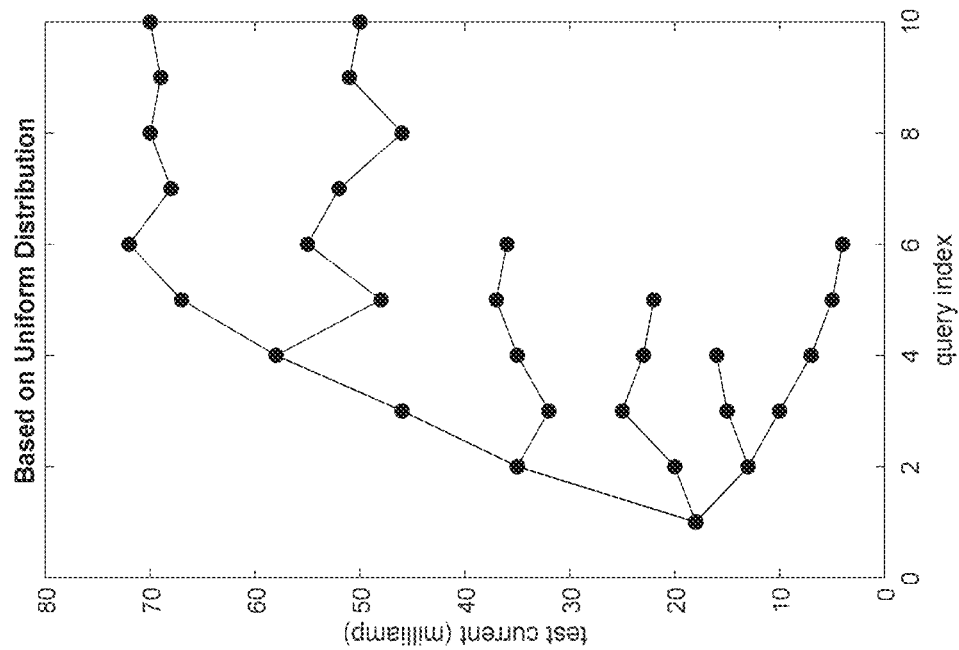
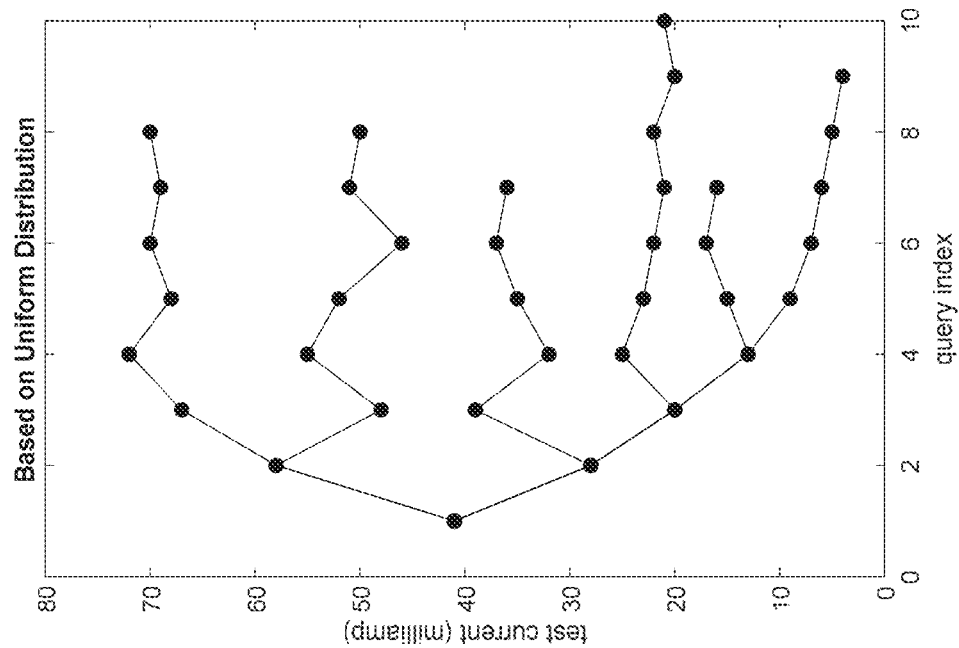
FIG. 13

INTELLIGENT DETERMINATION OF THERAPEUTIC STIMULATION INTENSITY FOR TRANSCUTANEOUS ELECTRICAL NERVE STIMULATION

REFERENCE TO PENDING PRIOR PATENT APPLICATIONS

This patent application:

(i) claims benefit of prior U.S. Provisional Patent Application Ser. No. 62/892,627, filed Aug. 28, 2019 by Neurometrix, Inc. and Rebecca A. Burrell et al. for METHOD AND APPARATUS FOR EFFICIENT DETERMINATION OF SENSATION THRESHOLD IN TRANSCUTANEOUS ELECTRICAL NERVE STIMULATOR; and (ii) claims benefit of prior U.S. Provisional Patent Application Ser. No. 62/776,834, filed Dec. 7, 2018 by Neurometrix, Inc. and Xuan Kong et al. for INTELLIGENT DETERMINATION OF THERAPEUTIC STIMULATION INTENSITY FOR TRANSCUTANEOUS ELECTRICAL NERVE STIMULATION.

The two (2) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes to provide symptomatic relief of pain. More specifically, this invention relates to apparatus and methods for setting up therapeutic stimulation intensity and therapeutic stimulation patterns based on: a TENS user's electro-tactile sensation threshold; demographic, clinical, and other relevant characteristics; contemporary progress of subjective and objective measures of pain relief, and therapeutic stimulation intensity and patterns preferred by other TENS users. This invention also discloses apparatus and methods for improving the estimation accuracy of a TENS user's electro-tactile sensation threshold.

BACKGROUND OF THE INVENTION

Transcutaneous electrical nerve stimulation (TENS) is the delivery of electricity across the intact surface of the skin to activate the underlying sensory nerve fibers and trigger various physiological responses. The most common clinical application of TENS is to provide analgesia, for acute or chronic pain. Unlike pharmacological approaches to pain control, TENS has few if any side effects and can be used as needed without supervision of a healthcare professional. There are additional clinical applications of TENS, including reduction in the symptoms of restless leg syndrome, decreased nocturnal muscle cramps, and relief from generalized pruritus. Preferred embodiments of the present invention focus on the treatment of chronic pain, which, for the purposes of the present invention, is considered to be pain on most days for at least 3 months. Common forms of chronic pain are arthritic pain such as in the knee or hip due to osteoarthritis, low back and leg pain such as due to lumbar disc disease or spinal stenosis, nerve pain such as due to diabetes, and generalized pain such as occurs with fibromyalgia.

In conventional TENS, electrodes are placed on the skin of the user within, adjacent to, or proximal to, the area of pain. In fixed-site high-frequency TENS, the electrodes are placed in an anatomically and physiologically optimal area (e.g., the upper calf of the user) that results in widespread analgesia. An electrical circuit generates stimulation pulses with specified characteristics. One or more pairs of electrodes, placed on the patient's skin, transduce the electrical pulses and thereby stimulate underlying nerves to relieve pain.

A conceptual model for how sensory nerve stimulation leads to pain relief was proposed by Melzack and Wall in 1965. Their theory proposes that the activation of sensory nerves (Aβ fibers) closes a "pain gate" in the spinal cord that inhibits the transmission of pain signals carried by nociceptive afferents (C and Aδ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the midbrain and medulla sections of the brainstem, respectively. The PAG has neural projections to the RVM, which in turn has diffuse bilateral projections into the spinal cord dorsal horn that inhibit ascending pain signal transmission.

TENS is typically delivered in short discrete pulses, with each pulse typically being several hundred microseconds in duration, at frequencies of between about 10 Hz and about 150 Hz, through hydrogel electrodes placed on the user's body. TENS is characterized by a number of electrical parameters including the amplitude and shape of the stimulation pulse (which combine to establish the pulse charge), the frequency and pattern of the stimulation pulses, the duration of a therapy session, and the interval between therapy sessions. All of these parameters are correlated to the therapeutic dose. For example, higher stimulation amplitude and longer stimulation pulses (i.e., larger pulse charges) increase the therapeutic dose, whereas shorter therapy sessions decrease the stimulation dose. Clinical studies suggest that pulse charge and therapy session duration have the greatest impact on therapeutic dose.

One of most important parameters for properly setting up TENS therapy is the electrical stimulation intensity (also known as the therapy intensity or the therapeutic intensity) which is generally associated with the amplitude of the electrical stimulation pulse. Current literature suggests that the electrical stimulation of TENS therapy should evoke "strong but not painful" sensation to maximize the therapeutic benefit of the TENS therapy. TENS users could seek professional help such as healthcare providers for proper setup of their TENS devices. However, access to such resources may be limited and inconvenient. Therapy outcome (e.g., reduction in pain intensity or pain interference to sleep) is gradual and sometimes hard to measure. Therefore, a TENS user may not be able to tell whether they are benefiting from therapies. The lack of positive and timely feedback often leads to premature termination of the TENS therapy and limits the therapeutic potential of TENS devices. FIG. 1 summarizes the process of traditional TENS applications.

Some over-the-counter TENS devices such as the Quell® product (Neurometrix Inc., Waltham, MA, USA) provide a two-step calibration process to help TENS users set up the proper therapeutic stimulation intensity. During the calibration process, the user will indicate their first sensation of electrical stimulation when the TENS device gradually ramps up the stimulation level. The user-indicated electro-tactile sensation threshold is then used by the TENS device to automatically set therapeutic stimulation intensity. FIG. 2 summarizes the process of TENS applications using this two-step therapy intensity setup. Further details of the two-step calibration process used by the aforementioned Quell® product are disclosed in U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION, issued as U.S. Pat. No. 8,948,876 on Feb. 3, 2015, which patent is hereby incorporated by reference. Like the process outlined in FIG. 1, the process lacks timely feedback such as the appropriateness of sensation threshold indication, therapy intensity setup, and outcome measure.

Two issues hinder proper setup of the therapeutic stimulation intensity: poor accuracy of the sensation threshold indicated by some users, and inter-subject variations of the relationship between sensation threshold and therapeutic intensity.

While most TENS users can accurately indicate their sensation threshold, some fail to indicate their sensation threshold correctly. Because sensation threshold indication is the first step to be performed after the TENS device and its associated electrodes are placed on the user's body, the sensation from elements such as the cold gel pads of the TENS electrodes may interfere with the user's perception of the electro-tactile stimulation sensation. As a result, the sensation threshold may be indicated by the user at too low or too high a level. Also, some users with prior experience of other TENS devices for which therapeutic intensity is directly set may incorrectly indicate a desired therapeutic intensity instead of the true sensation threshold, resulting in an indicated sensation threshold which is higher than the actual sensation threshold. It is thus important, when using the aforementioned two-step therapy intensity setup, to validate the sensation threshold in real time prior to its use in calculating the therapeutic intensity. It is also desirable to provide an immediate feedback to the user if the indicated sensation threshold is outside an expected range.

While the sensation threshold is the most important predictor of TENS therapeutic intensity for an individual, other factors (such as age, gender, health conditions, chronic pain history, etc.) also affect the therapeutic stimulation intensity which is optimal to individual TENS users. Lack of personalization of mapping a user-indicated sensation threshold to the desired therapeutic intensity may lead to sub-optimal setting of therapeutic intensity. TENS users must then manually adjust their therapeutic intensity levels through trial and error, a time-consuming process. Therefore, it is desirable to create a personalized mapping, from sensation threshold to therapeutic intensity, based on characteristics of each TENS user.

SUMMARY OF THE INVENTION

The present invention comprises the provision and use of a novel apparatus and method to maximize the therapeutic benefits of TENS therapy for individual users. Function blocks of the present invention are illustrated in FIG. 3. Specifically, present invention discloses an efficient and versatile means to allow users to indicate their sensation threshold based on a probabilistic bisection algorithm and other search algorithms (705, FIG. 3). The present invention further discloses a means to validate a user-indicated sensation threshold by assigning a confidence level to the user-indicated sensation threshold based on a user profile and other factors (715, FIG. 3). Additionally, the present invention discloses a means to set up the therapeutic intensity based on a combination of factors such as the user-indicated sensation threshold, user profile, time course to reach the user-indicated sensation threshold, and the confidence level for the sensation threshold indication (710, FIG. 3). The present invention also discloses a means to leverage therapy utilization tracking and objective outcome measures to adjust the therapeutic intensity setup based on a similarity score between an individual user profile and data in a connected health cloud database (720, FIG. 3). The health cloud database includes records from multiple TENS users, with the fields preferably comprising user profile, therapeutic intensity setup, therapy utilization tracking, objective and subjective outcome measures, and other chronic pain indicators (725, FIG. 3). The present invention also discloses methods to manage the health cloud database so that different weights are assigned to different records in the health cloud database when the records are used to derive a therapeutic intensity setup recommendation for each individual TENS user.

In one form of the invention, there is provided apparatus for determining a target stimulation intensity level of transcutaneous electrical nerve stimulation to a user that evokes a desired sensation from the user, said apparatus comprising:
a stimulation unit for electrically stimulating at least one nerve of the user;
a control unit for determining an intensity level of a next electrical stimulation to be delivered to the user by the stimulation unit based on a likelihood function for a range of intensity levels to be the target intensity level;
an indication unit for enabling the user to indicate when a desired sensation is felt when the stimulation unit stimulates the user at a given intensity level; and
a calculation unit for updating a likelihood function for a range of intensity levels to be the target intensity level to evoke the desired sensation from the user;
wherein the control unit is configured to establish the target stimulation intensity level at the intensity level at which the likelihood function is maximum and the maximum likelihood value exceeds a threshold value.

In another form of the invention, there is provided apparatus for assessing the accuracy of a target stimulation intensity level used in transcutaneous electrical nerve stimulation to a user, said apparatus comprising:
a calculation unit for calculating a set of expected values of the target stimulation intensity level for a desired sensation based on a profile of the user;
a stimulation unit for electrically stimulating at least one nerve of the user at one or more stimulation levels;
a discovery unit for enabling the user to indicate a target stimulation intensity level at which the electrical stimulation to the user evokes the desired sensation from the user; and
an assessment unit to determine the accuracy of the indicated target stimulation intensity level based on the expected set of values of the target stimulation intensity level for the desired sensation.

In another form of the invention, there is provided apparatus for providing transcutaneous electrical nerve stimulation to a user, said apparatus comprising:
an indication unit for enabling the user to indicate when an intensity level of an electrical stimulation delivered to the user meets the user's sensation threshold;
a prediction unit for predicting a therapeutic intensity of transcutaneous electrical nerve stimulation for the user; and
a stimulation unit for electrically stimulating at least one nerve of the user with the predicted therapeutic intensity of transcutaneous electrical nerve stimulation;

wherein the predicted therapeutic intensity depends upon a user profile and a scaling factor applied to the sensation threshold of the user, and further wherein the scaling factor varies with a confidence level of the sensation threshold of the user.

In another form of the invention, there is provided apparatus for providing transcutaneous electrical nerve stimulation to a user, said apparatus comprising:

a prediction unit for predicting a therapeutic intensity of transcutaneous electrical nerve stimulation for the user; and a stimulation unit for electrically stimulating at least one nerve of the user with the predicted therapeutic intensity of transcutaneous electrical nerve stimulation; and a monitoring unit for monitoring an outcome of electrically stimulating the user with the predicted therapeutic intensity over a time period;

wherein the prediction unit modifies its predicted therapeutic intensity for the user based on the monitored outcome from the monitoring unit.

In another form of the invention, there is provided a system for providing transcutaneous electrical nerve stimulation to a user, said system comprising:

a database comprising information regarding a plurality of people, wherein the information comprises, for each person in the database, a profile, a time course of electrical stimulation characteristics, and a therapeutic outcome;

a prediction unit for predicting a sequence of therapeutic intensity levels of transcutaneous electrical nerve stimulation over time for the user; and a stimulation unit for electrically stimulating at least one nerve of the user with the predicted sequence of therapeutic intensity levels over time;

wherein the predicted sequence of therapeutic intensity levels depends upon (i) a user profile and a desired therapeutic outcome of the user, and (ii) the information in the database.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view of the progression of querying current intensity as a function of query steps when the initial sensation threshold profiles corresponding to those of FIG. 6 are used.

DETAILED DESCRIPTION OF THE PREFERRED EMBODIMENTS

The TENS Device in General

Figure 1:
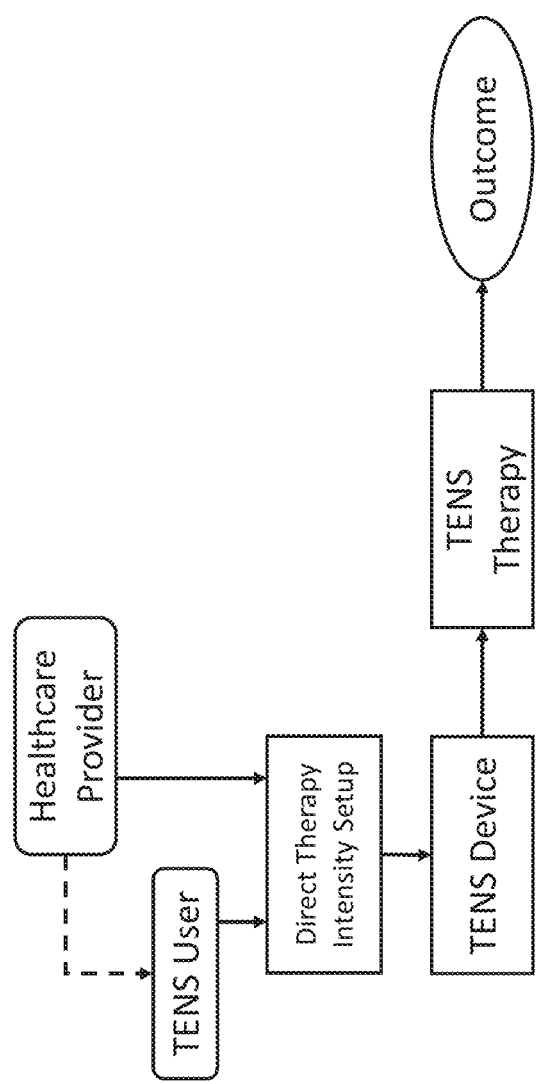
FIG. 1 is a flowchart showing how to set up a TENS device by directly adjusting therapy intensity.
Figure 2:
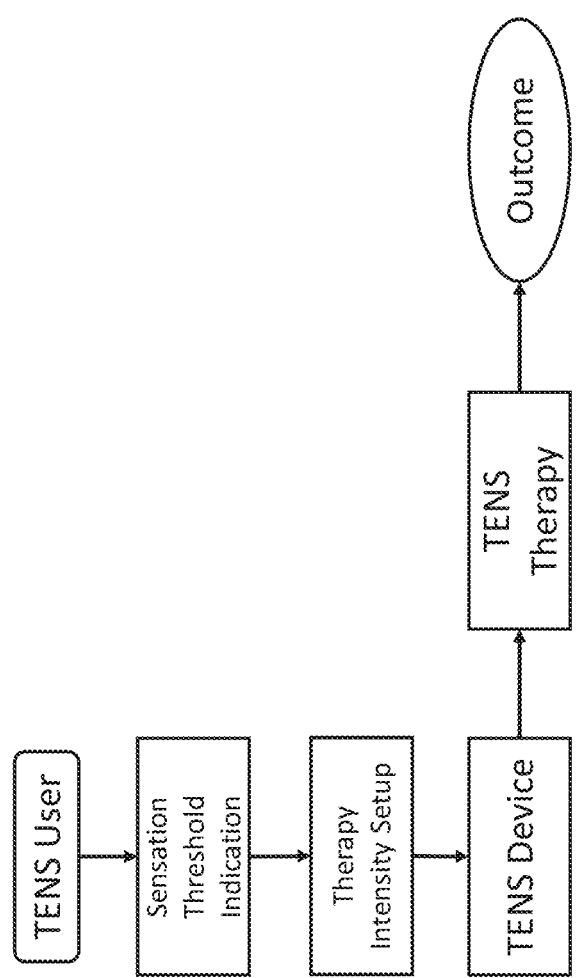
FIG. 2 is a flowchart showing how to set up a TENS device by determining therapy intensity based on a user-indicated sensation threshold (i.e., using the aforementioned two-step therapy intensity setup procedure—note that the TENS therapy outcome is not used to further adjust therapy intensity setup)
Figure 3:
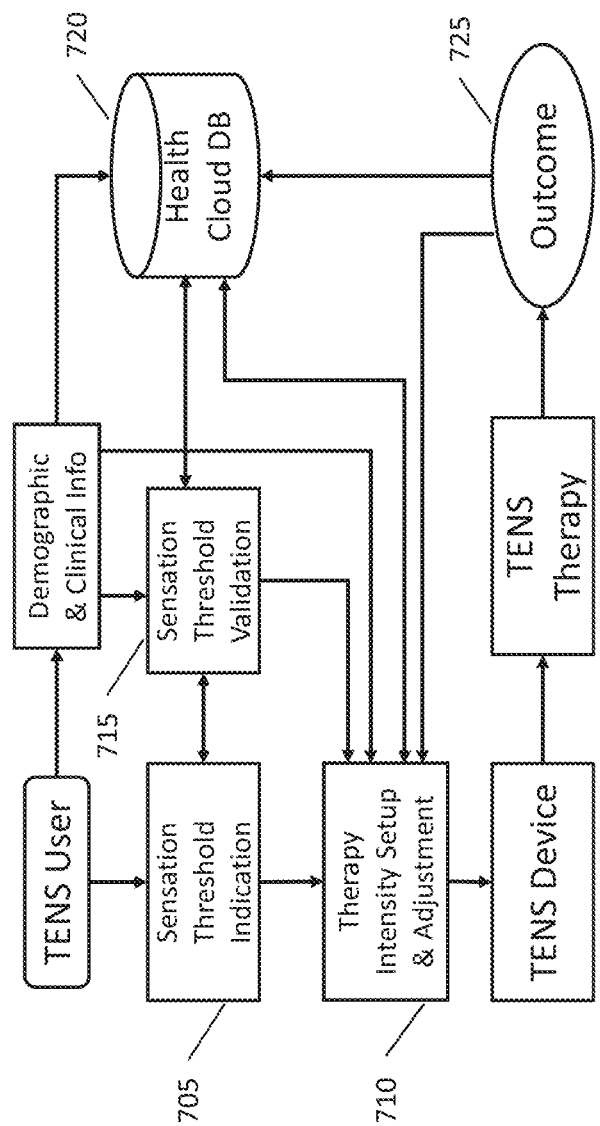
FIG. 3 is a flowchart showing an exemplary construction of the present invention to intelligently set up a TENS device based on a user-indicated sensation threshold, a TENS user profile (demographic and clinical information), therapy outcome measures, and a set of data from a health cloud database.

The present invention comprises the provision and use of a novel TENS device comprising a stimulator designed to be placed on a user's upper calf (or other anatomical location) and a pre-configured electrode array designed to provide electrical stimulation to at least one nerve disposed in the user's upper calf (or other anatomical location). Although the preferred embodiment of the present invention comprises the placement of the TENS device on the upper calf of the user, additional anatomical locations (such as above the knee, on the lower back, and on the upper arm) are contemplated and are also considered to be within the scope of the present invention.

There are various forms of TENS that are primarily differentiated by stimulation characteristics. The most common forms of TENS is "conventional TENS". In a conventional TENS device, an electrical circuit generates repetitive, discrete stimulation pulses. The pulse waveform specifications include amplitude (usually up to 100 mA), duration (typically 100-500 μsec) and shape (typically monophasic or biphasic). The pulse sequence specifications include the frequency (typically 50-150 Hz) and pattern (e.g., regular, random, bursts). Finally, the therapy schedule is defined by the duration of each therapy session (typically 20-60 minutes of continuous stimulation), and the interval between therapy sessions, which is usually manually controlled by the user but which may be automated (typically every 30-60 minutes). One or more pairs of electrodes, placed on the patient's skin, transduce the electrical pulses provided by the stimulator and thereby stimulate underlying nerves. The clinical efficacy, comfort and efficiency of TENS is dependent on the aforementioned stimulation parameters. For example, to be effective, the stimulation intensity must be above the sensation threshold at a level that feels "strong but comfortable" to the user. Therapy sessions having a length of 60 minutes are more effective than shorter sessions. Finally, the therapy schedule should match the user's pain pattern, which may require therapy sessions throughout the day and night.

While the stimulation intensity is normally associated with the amplitude of an electrical stimulation pulse, the term "intensity" in this application is more generally used to refer to any stimulation characteristics that may impact the effect of electrical pulses on a TENS user or any combination of these characteristics. The characteristics may include the amplitude of an individual stimulation pulse, the width of each pulse, the morphology of the pulse (e.g., rectangular, triangle, trapezoid), the complexity of the pulse (e.g., one rectangular shape followed by another rectangular shape of opposite polarity), the asymmetry of complex pulses (e.g., a second rectangular shape following a first rectangular shape may have its width, or height, or both, different from that of the first rectangular shape), the frequency of the pulses (e.g., fixed or random), patterns of the pulses (e.g., pulses with regular intervals between consecutive pulses (regular) or a group of several pulses with very short intervals between them and then separated by a long interval before another group of pulses is activated (burst)), and the therapy session duration (how long each active stimulation session lasts). The duration of a pulse is the same as the width of the pulse if only one simple geometric shape is in the pulse. The duration of a pulse with two rectangular shapes separated by a quiet period is the summation of the widths of the two rectangular shapes.

Figure 4:
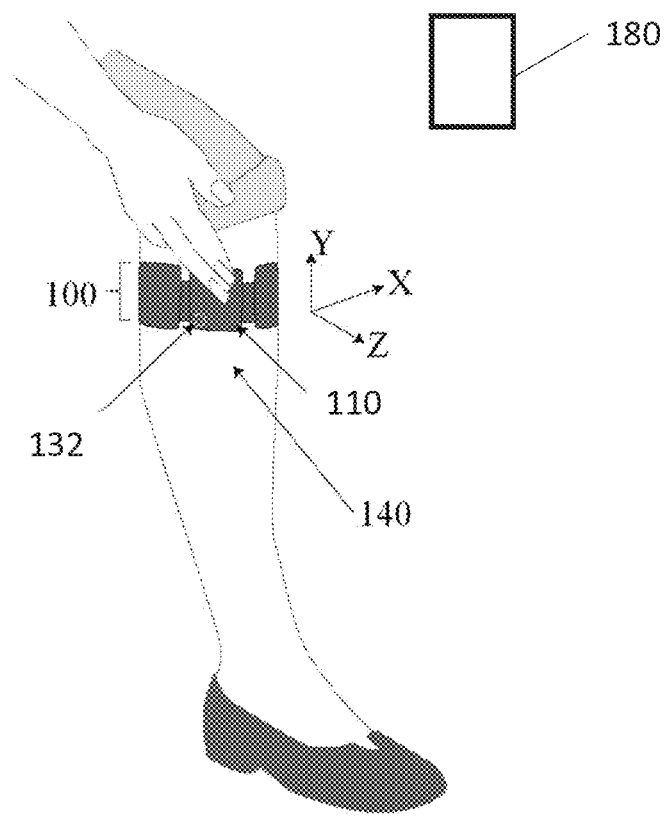
FIG. 4 is a schematic view showing a novel TENS device formed in accordance with the present invention, wherein the TENS device is mounted to the upper calf of a user and a remote unit (e.g., a smartphone or tablet) allows interactions with the TENS device, either manually or automatically.

More particularly, and looking now at FIG. 4, there is shown a novel TENS device 100 formed in accordance with the present invention, with novel TENS device 100 being shown worn on a user's upper calf 140. A user may wear TENS device 100 on one leg or on both legs (either one at a time or simultaneously), or a user may wear a TENS device 100 on another area of the body separate from, or in addition to, a TENS device 100 worn on one leg (or both legs) of the user.

Figure 5:
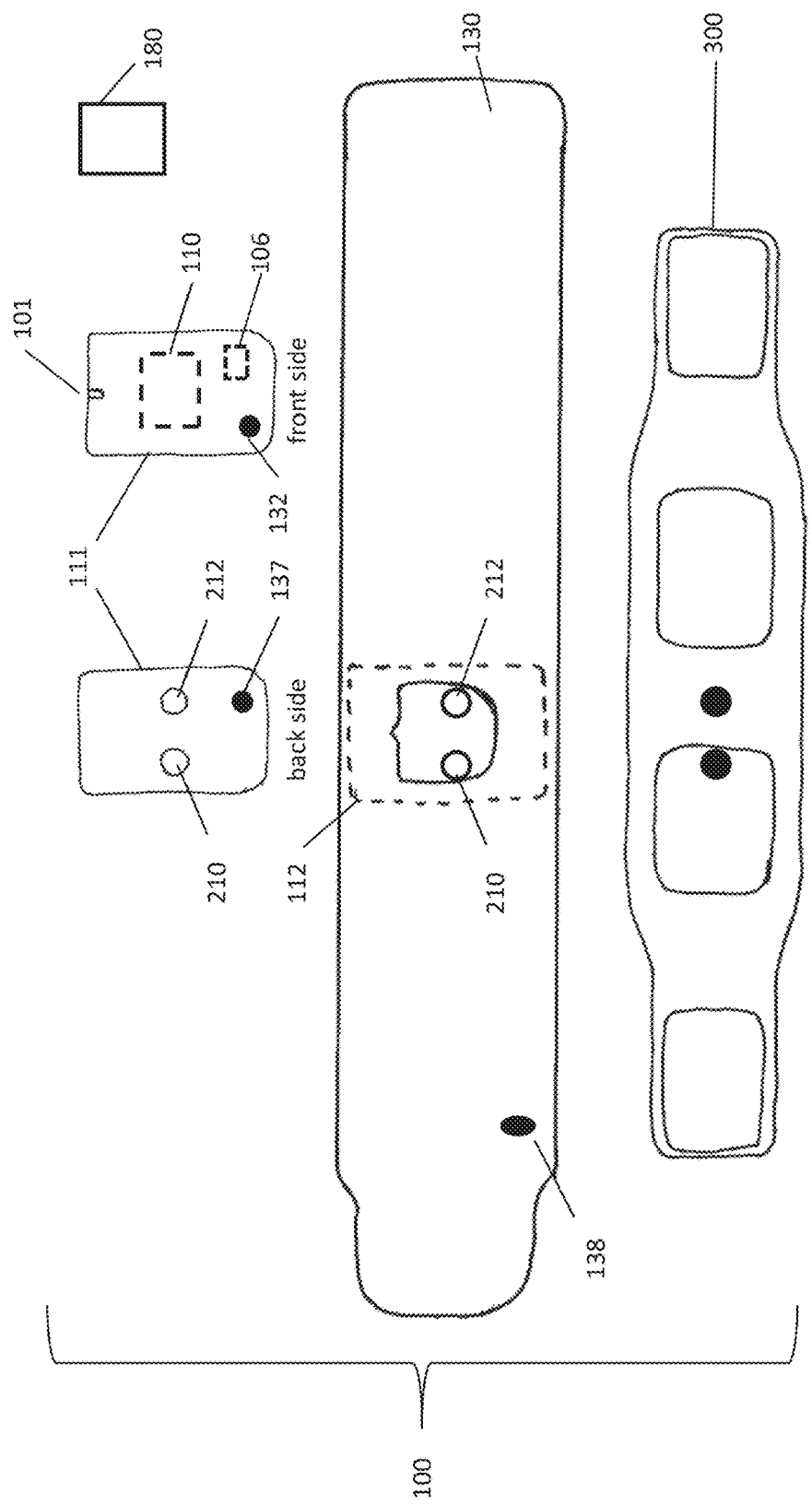
FIG. 5 is a schematic view showing the novel TENS device of FIG. 4 in greater detail.
Figure 7:
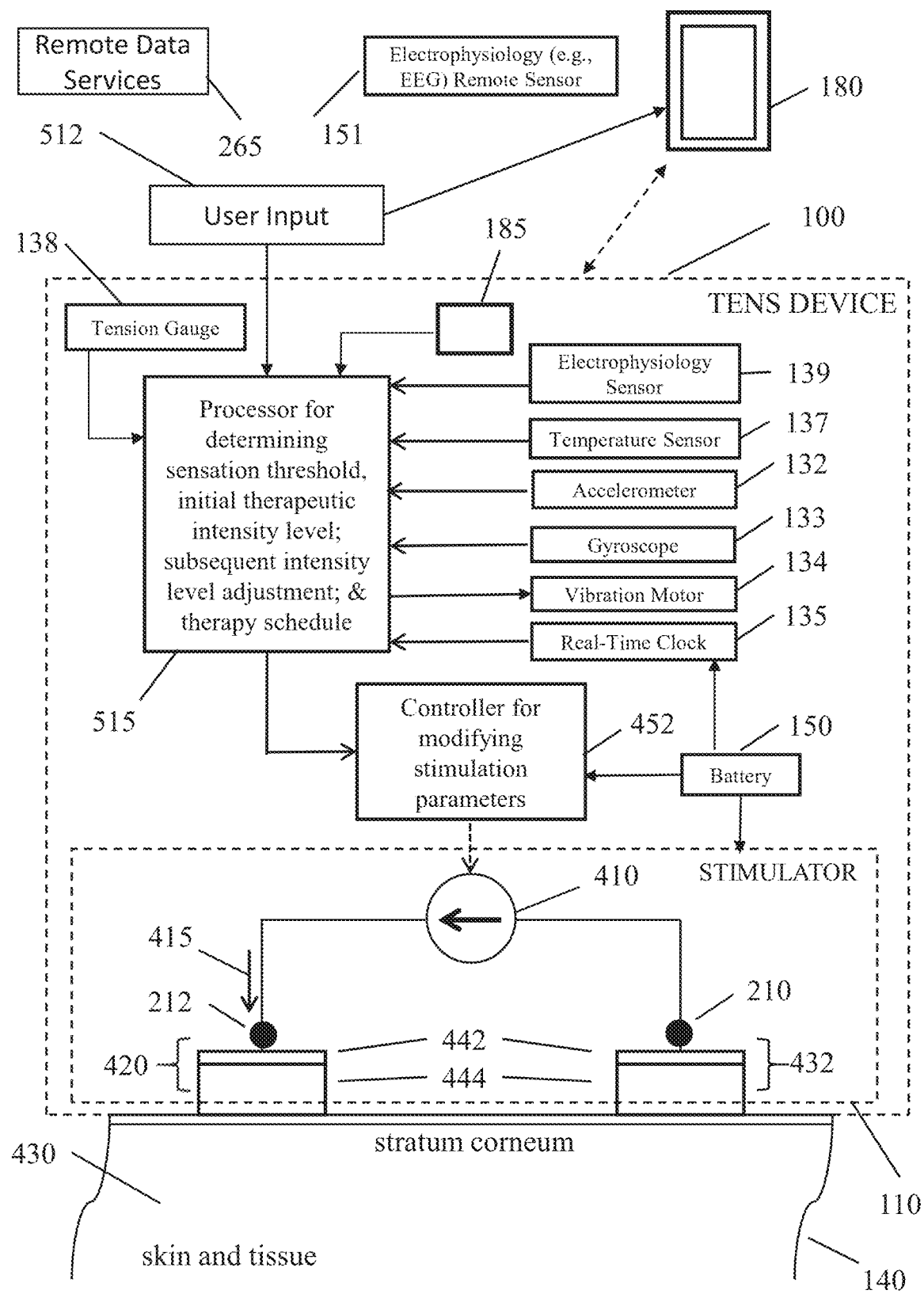
FIG. 7 is a schematic view of the novel TENS device of FIGS. 3-6, including a processor for determining sensation threshold, initial therapeutic intensity level, subsequent intensity level adjustment, and therapy schedule.

Looking next at FIG. 5, TENS device 100 is shown in greater detail. TENS device 100 preferably comprises three primary components: a stimulator 110, a strap 130, and an electrode array 300 (comprising a cathode electrode and an anode electrode appropriately connected to stimulator 110). It will be appreciated that strap 130 carries stimulator 110 and electrode array 300, with stimulator 110 and electrode array 300 being electrically interconnected and strap 130 is intended to be mounted to the body of a user so that electrode array 300 contacts an appropriate skin surface. In a preferred form of the present invention, a stimulator housing 111 houses the TENS stimulation circuitry, and one or more user interface elements 101 (e.g., an LED) and 106 (e.g., a push button) of stimulator 110. Both the front side and the back side of stimulator housing 111 are shown in FIG. 5. Strap 130 comprises a pocket 112 for receiving stimulator housing 111 of stimulator 110. TENS device 100 preferably also comprises an accelerometer 132 (see FIGS. 5 and 7), preferably in the form of a MEMS digital accelerometer microchip (e.g., Freescale MMA8451Q), for detecting (i) user gestures such as taps to stimulator housing 111, (ii) user limb and body orientation (when device 100 is disposed on the user's skin), and (iii) user limb and body motion (when the device is disposed on the user's skin). Note that accelerometer 132 may be located within or outside stimulator housing 111. Accelerometer 132 also monitors the motion and orientation of the TENS device when the TENS device is not placed on the body of a user. TENS device 100 also comprises a gyroscope 133 (FIG. 7), a vibration motor 134 (FIG. 7), a real-time clock 135 (FIG. 7), a temperature sensor 137 (FIGS. 5 and 7), a galvanic skin response (GSR) sensor which is preferably a part of an electrophysiology sensor 139 (FIG. 7), and a strap tension gauge 138 (FIGS. 5 and 7). Note that the above-referenced elements such as gyroscope 133, temperature sensor 137, GSR/electrophysiology sensor 139 and/or vibration motor 134 may be located within or outside stimulator housing 111 (e.g., they may be located on the strap 130).

In one preferred form of the invention, stimulator housing 111 also houses a battery 150 (FIG. 7) for powering the TENS stimulation circuitry and other circuitry, and other ancillary elements, such as a wireless link module 185 (FIG. 7) of the sort well known in the art of wireless communications for allowing TENS device 100 to wirelessly communicate with a remote controller 180 (e.g., a hand-held electronic device such as a smartphone or tablet, or a RFID (radio frequency identification) tag, see FIG. 7) or a remote data service 265 (e.g., a health cloud database that contains data from other TENS users. The remote controller 180 is also capable of receiving user input (such as a tap on the controller screen) to indicate the electro-tactile sensation of a stimulation, etc.

In another form of the invention, TENS device 100 may comprise more than one stimulator housing 111, e.g., to better conform to the body and/or to improve user comfort by distributing circuitry and portable power source components more evenly around the perimeter of a leg (or other body part).

And in still another form of the invention, a flexible circuit board is used to distribute the TENS stimulation circuitry and other circuitry more evenly around the leg of the user and thereby reduce the thickness of the device.

Looking now at FIG. 5, interface element 106 preferably comprises a push button for user control of electrical stimulation. In another embodiment, user control of electrical stimulation and user indication of electrotactile sensation are effected through intentional gestures (e.g., taps) without the need of a physical button (i.e., without the need for a mechanical actuator). For example, in one form of the invention, a three-axis accelerometer is incorporated into the TENS device and measures the motion and orientation of the TENS device caused by user gestures such as taps, flicks, and shakes. Gestures could also be in the form of some gross body movement, such as swinging a leg back and forward or left and right. The gestures are used to control the device states and operations accordingly (e.g., registering a sensation threshold, stopping electrical stimulation, etc.). Other user interface control means may be provided for controlling the state and operation of the TENS device via wireless connections, e.g., an "App" running on a Bluetooth-enabled smartphone or tablet, or an RFID tag and other near-field communication devices.

The same push button or any other user input means can serve more than one function through context-based interpretation. For example, during the calibration process, a gentle tap to the device housing can serve as an indication of sensing the current stimulation pattern; during "standby" state, the same tap can serve as a start command to initiate a TENS therapy; and during active stimulation state, the same tap can serve as a stop command to stop the ongoing TENS therapy.

Still looking at FIG. 5, user interface element 101 preferably comprises an LED for indicating stimulation status and for providing other feedback to the user. Although a single LED is shown in FIG. 5, user interface element 101 may comprise multiple LEDs with different colors. Additional user interface elements (e.g., a multi-LED array, an LCD display, audio feedback through a beeper or voice output, haptic devices such as a vibrating element, a smartphone running an appropriate "App", etc.) are also contemplated and are considered to be within the scope of the present invention.

In one preferred form of the invention, TENS device 100 is configured to be worn on the user's upper calf 140 as is shown in FIG. 4, although it should be appreciated that TENS device 100 may also be worn on other anatomical locations, or multiple TENS devices 100 may be worn on various anatomical locations, etc. TENS device 100 (comprising the aforementioned stimulator 110, electrode array 300, and strap 130, assembled together as a unit) is secured to upper calf 140 (or other anatomical location) of the user by placing TENS device 100 in position against the upper calf (or other anatomical location) of the user and then tightening strap 130. In one preferred form of the invention, electrode array 300 is sized and configured so that it will apply appropriate electrical stimulation to the appropriate anatomy of the user regardless of the specific rotational position of TENS device 100 on the leg (or other anatomical location) of the user.

In another preferred form of the invention, TENS device elements 110, 300, and 130 are integrated into one element.

Figure 6:
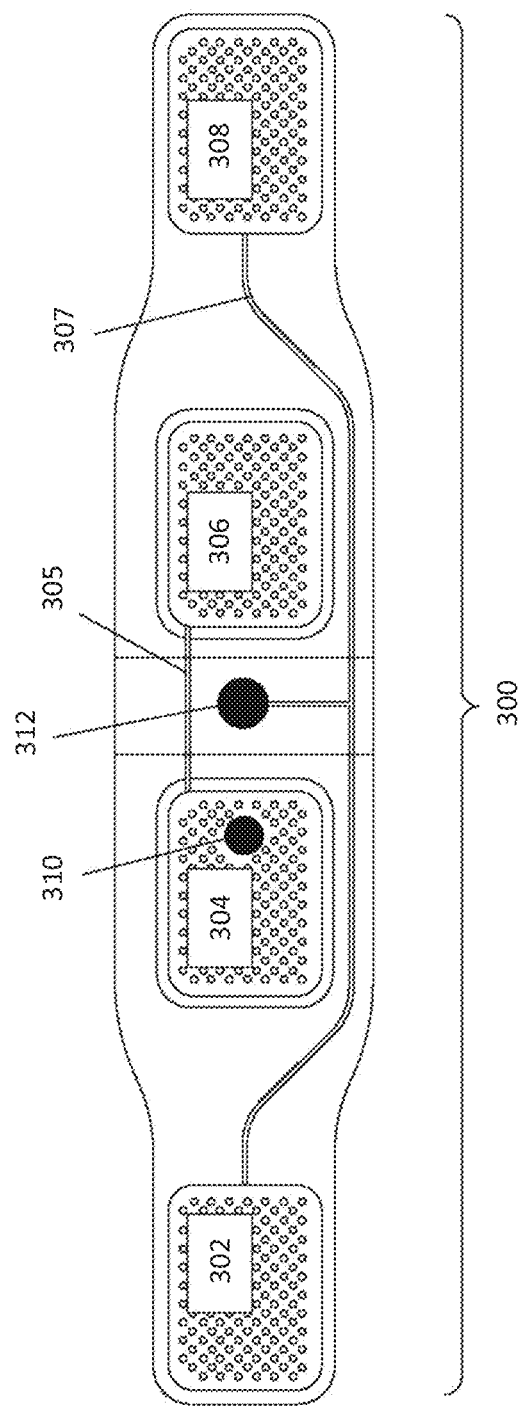
FIG. 6 is a schematic view showing the electrode array of the novel TENS device of FIGS. 4 and 5 in greater detail.

FIG. 6 shows a schematic view of one preferred form of electrode array 300. Electrode array 300 preferably comprises four discrete electrodes 302, 304, 306, 308, each having an equal or similar size (i.e., an equal or similar size surface area). Electrodes 302, 304, 306, 308 are preferably connected in pairs so that electrodes 304 and 306 (representing the cathode of TENS device 100) are electrically connected to one another (e.g., via connector 305), and so that electrodes 302 and 308 (representing the anode of TENS device 100) are electrically connected to one another (e.g., via connector 307). It should be appreciated that electrodes 302, 304, 306, 308 are preferably appropriately sized, and connected in pairs, so as to ensure adequate skin coverage regardless of the rotational position of TENS device 100 (and hence regardless of the rotational position of electrode array 300) on the leg (or other anatomical location) of a user. Furthermore, it should be appreciated that electrodes 302, 304, 306, 308 are not connected in an interleaved fashion, but rather are connected so that the two inside electrodes 304, 306 are connected to one another, and so that the two outside electrodes 302, 308 are connected to one another. This electrode connection pattern ensures that if the two outer electrodes 302, 308 should inadvertently come into contact with one another, an electrical short of the stimulation current flowing directly from cathode to anode will not occur (i.e., the electrode connection pattern ensures that the therapeutic TENS current is always directed through the tissue of the user).

Electrical current (i.e., for therapeutic electrical stimulation to the tissue) is provided to the electrode pairs 304, 306 and 302, 308 by connectors 310, 312 (FIG. 6) which mate with complementary connectors 210, 212 (FIGS. 5 and 7), respectively, on stimulator 110. Stimulator 110 generates electrical currents that are passed through electrodes 304, 306 and electrodes 302, 308 via connectors 310, 312, respectively.

In one preferred form of the present invention, the skin-contacting conductive material of electrodes 302, 304, 306, 308 is a hydrogel material which is "built into" electrodes 302, 304, 306, 308. The function of the hydrogel material on the electrodes is to serve as an interface between the electrodes 302, 304, 306, 308 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated and are considered to be within the scope of the present invention.

FIG. 7 is a schematic representation of TENS device 100 and, among other things, the current flow between TENS device 100 and the user. As seen schematically in FIG. 7, stimulation current 415 from a constant current source 410 flows into the user's body tissue 430 (e.g., the user's upper calf) via an anode electrode 420 (which anode electrode 420 comprises the aforementioned electrodes 302, 308). Anode electrode 420 comprises a conductive backing (e.g., silver hatch) 442 and hydrogel 444. The current passes through the user's tissue 430 and returns to constant current source 410 through cathode electrode 432 (which cathode electrode 432 comprises the aforementioned electrodes 304, 306). Cathode electrode 432 also comprises a conductive backing 442 and hydrogel 444. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

As shown in FIG. 7, TENS device 100 comprises a controller 452 for controlling the operation of constant current source 410. Controller 452 may be used to adjust stimulation current 415 so as to modify one or more stimulation parameters, e.g., stimulation pulse intensity, stimulation pulse width, stimulation pulse frequency, therapy session duration, the time delay between therapy sessions, etc.

As shown in FIG. 7, TENS device 100 also comprises a processor 515 for determining various operating parameters of TENS device 100 (e.g., sensation threshold, initial therapeutic intensity level, subsequent intensity level adjustment, therapy schedule, etc.) and operating controller 452 so as to provide the desired stimulation current 415. More particularly, processor 515 receives data inputs from (i) various sensors of TENS device 100 (e.g., data from electrophysiology sensor 139, temperature sensor 137, accelerometer 132, gyroscope 133, real-time clock 135, tension gauge 138, etc.), and (ii) user inputs 512 (e.g., user taps on stimulator housing 111, user "pushes" on push button 106, user inputs via an App running on smartphone or tablet 180, etc.), and operates the aforementioned controller 452 so as to cause constant current source 410 to provide the desired stimulation current 415. Processor 515 can also be used to drive vibration motor 134. Mechanical vibrations from motor 134 can serve as a means of feedback to the user. The vibrations can also serve as stimuli to suppress pain in a manner similar to using a hand to rub a skin area to reduce pain.

It should be appreciated that processor 515 may comprise a general purpose microprocessor (CPU) of the sort well known in the art together with appropriate programming to provide the functionality disclosed herein, including, among other things, providing the functionality for determining sensation threshold, the functionality for determining initial therapeutic intensity level, the functionality for determining subsequent intensity level adjustment, the functionality for determining the therapy schedule, etc.

Figure 8:
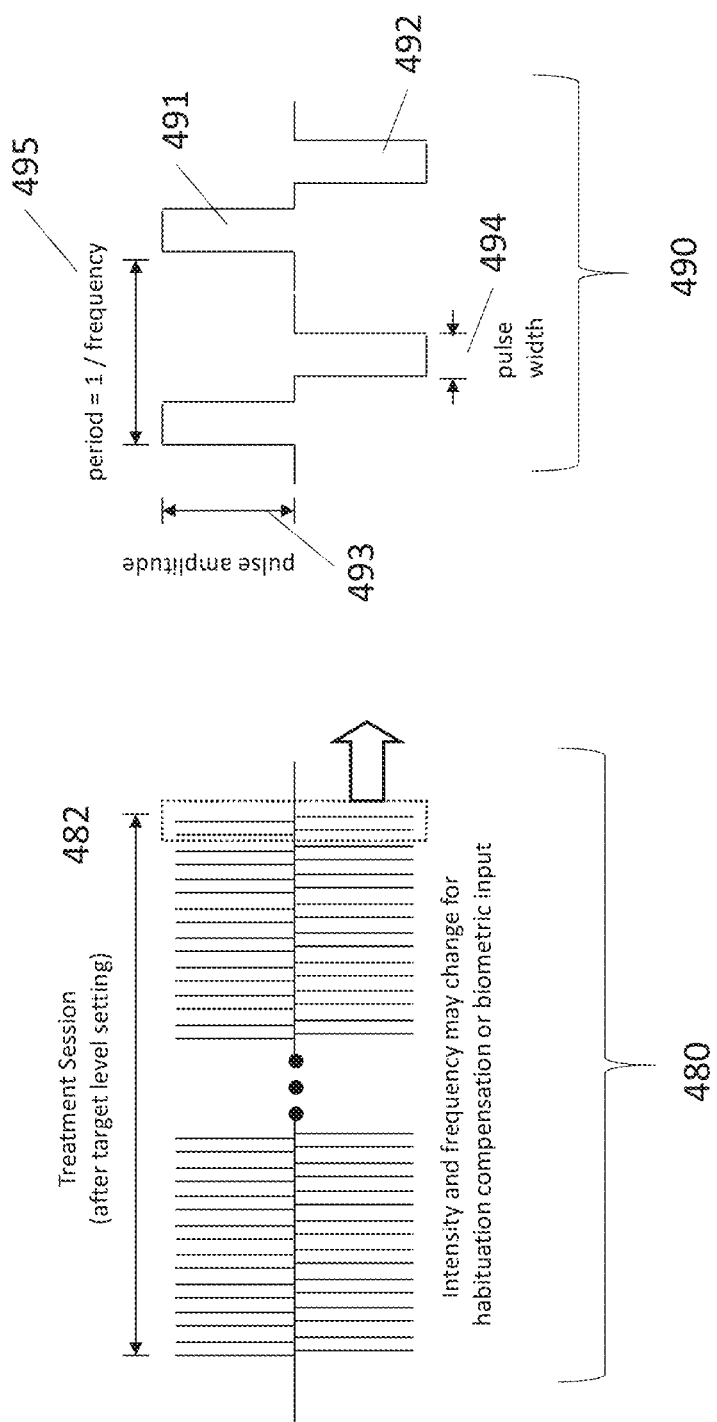
FIG. 8 is a schematic view showing a stimulation pulse train generated by the stimulator of the novel TENS device of FIGS. 3-7.

FIG. 8 is a schematic view showing a pulse train 480 provided by stimulator 110 during a TENS therapy session, and the waveform 490 of two individual biphasic pulses, wherein each individual biphasic pulse comprises a first phase 491 and a second phase 492. In one form of the invention, each pulse waveform is charge-balanced across the two phases 491 and 492 of the biphasic pulse, which prevents iontophoretic build-up under the electrodes of the electrode array 300 that can lead to skin irritation and potential skin damage. In another form of the invention, the individual pulses are unbalanced across the two phases of the biphasic pulse, however, charge-balancing is achieved across multiple consecutive biphasic pulses. Pulses of fixed or randomly-varying frequencies are applied throughout the duration of the therapy session 482. The intensity of the stimulation (i.e., the amplitude 493 of the current delivered by stimulator 110) is adjusted in response to: user input (including the user-indicated sensation threshold); the user profile (including demographic and clinical characteristics); the utilization patterns of the user; subjective feedback from the user on the efficacy of TENS therapies; objective measures such as sleep duration, sleep quality, activity level, and gait stability; and the quantifiable relationship between the benefits and outcomes of other TENS users and their TENS device setup and usage patterns, as will hereinafter be discussed in further detail.

In prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION, issued as U.S. Pat. No. 8,948,876 on Feb. 3, 2015, which patent is hereby incorporated herein by reference, apparatus and methods are disclosed for allowing a user to personalize the TENS therapy stimulation intensity according to the electrotactile perception threshold of the user at the time of the setup of the TENS device. The aforementioned U.S. Pat. No. 8,948,876 also discloses apparatus and methods to automatically restart additional therapy sessions after an initial manual start by the user.

In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, which patent is hereby incorporated herein by reference, apparatus and methods are disclosed which allow for the safe delivery of TENS therapies at night when the user is asleep. These methods and apparatus allow the TENS device to be worn by a user for an extended period of time, including 24 hours a day.

There is no single (i.e., universal) TENS stimulation intensity that provides an effective, yet tolerable (i.e., not painful), therapeutic dose for all users. Therefore, in order to obtain the clinical benefit of TENS therapy, it is essential to set the therapeutic stimulation intensity to a user-specific level. A stimulation intensity that elicits a "strong but not painful" sensation will provide effective pain relief, and is therefore suggestive of an intensity that is within the therapeutic window. The traditional approach in TENS is for medical staff to train TENS users (i.e., patients) on how to manually increase the intensity until they perceive the "strong but not painful" sensation. It is then the responsibility of the user to perform this procedure as necessary, e.g., at home when TENS therapy is needed. In addition to using expensive and often inaccessible medical resources, this approach is error prone inasmuch as users may forget how to determine an appropriate therapeutic intensity. A major objective of the present invention is, therefore, to automatically and reliably set the stimulation intensity within the therapeutic range.

The present invention discloses a method for automatically setting the stimulation intensity to a therapeutic level with a sensation that is "strong but not painful". The method is based on the concept of mapping the user's electrotactile perception scale, on which the "strong but not painful" sensation is represented, to an electrical stimulation intensity scale as measured in milliamps. In this respect, the term "electrotactile" refers to a user's sensation of electrical stimulation. There are three key measurable electrotactile perception levels: the electrotactile sensation threshold (electrotactile sensation threshold refers to the first sensation of electrical stimulation by a user), the electrotactile pain threshold (electrotactile pain threshold refers to the first pain sensation by a user as a result of electrical stimulation), and the electrotactile tolerance threshold (electrotactile tolerance threshold is the maximum electrotactile pain sensation that a user will tolerate voluntarily). An optimal TENS stimulation intensity is between the electrotactile sensation threshold and the electrotactile pain threshold.

Although the identification of the electrotactile sensation threshold is the primary focus of the preferred embodiment as described in this application, it should be understood that the identification of other target thresholds or desired sensations (such as the electrotactile pain threshold, the electrotactile tolerance threshold, the strong but not painful sensation level, and the strong but comfortable sensation level) are equally applicable with the method described in this application.

Probabilistic Bisection Search Model for Indicating Sensation

The problem of identifying the stimulation intensity threshold at which a user can sense the stimulation can be formulated as a task of finding the position of a target value within a sorted array. The target value is the minimum intensity level that can be perceived reliably by a user. The sorted array is a list of ordered intensity levels where the order is based on the likelihood that the stimulation intensity will invoke an electrotactile sensation from a user. The most efficient search algorithm is a binary search algorithm. However, the decision of labeling each intensity level as either above or below the electrotactile sensation threshold is not perfect (i.e., the process is noisy, with a certain level of error rate). Probabilistic bisection search algorithms (also known as noisy binary search algorithms) are designed to deal with the situation where the algorithm cannot reliably compare elements of the array or label elements with certainty.

The preferred embodiment of the present invention uses the probabilistic bisection search algorithm to determine the electrotactile sensation threshold based on a user's reaction to the presentation of a collection of electrical stimulation pulses with different stimulation intensity levels.

It can be shown that the optimal method of finding a unique point $X^*$ (the electrotactile sensation threshold intensity for an individual) in a range $\mathbb{R}$ (all of the possible sensation threshold intensity values or the stimulation intensity range of the TENS device) is a bisection algorithm, in which a perfect information source is queried repeatedly to learn whether a given point x is to the left or the right of $X^*$. This has the effect of halving the size of the search space at each iteration. However, if the information source is imperfect, i.e., responses from the information source are noisy, and therefore only correct with some probability p, where $\frac{1}{2}<p<1$, then the bisection algorithm may choose the wrong path at any iteration, leading to an incorrect result. In the context of calibration, some TENS users are unable to consistently indicate correct classifications as to whether a given stimulation intensity is above or below electrotactile sensation. Therefore, it is important to develop apparatus and method to robustly estimate sensation threshold under the assumption that user indications may be incorrect from time to time.

Probabilistic Bisection Algorithm (PBA)

To account for a noisy or imperfect response from TENS users during a calibration process, we can modify the binary search approach such that at each iteration, we bisect the probability space of $\mathbb{R}$ instead, using Bayes' rule to update the posterior probability density (R. Waeber, P. Frazier, and S. Henderson. Bisection Search with Noisy Responses. In SIAM Journal on Control and Optimization. May 20, 2013; 51(3)). In the general case, we can assume that the probability density function (PDF) Fn is a uniform distribution over $\mathbb{R}$. However, later results will show that we can achieve a more accurate and faster-converging calibration with a distribution that approximates the PDF of the sensation threshold (ST) over the user population or the PDF of the ST tailored to an individual based on demographic and clinical characteristics (i.e., user profile).

After each iteration n, the median of the cumulative density function Fn provides a new estimate of X* for the (n+1)th query. It can be shown that the residuals, $\varepsilon[|X^*-X_n|]$, converge to 0 at a geometric rate or better. For each iteration, the user provides a response as to whether he has sensed the stimulation at a given intensity $X_n$, $Z_n(X_n) \in \{-1,+1\}$. The result $Z_n(X_n)=+1$ (not able to sense the stimulation) indicates X* is to the right of $X_n$, and $Z_n(X_n)=-1$ indicates X* is to the left of $X_n$ (able to sense the stimulation). Z can be thought of as a random Bernoulli variable.

In a preferred embodiment of the present invention, we consider the user's indication as noisy responses to queries and individual test currents (i.e., various stimulation currents provided by TENS device 100) to be the queries. The user is instructed to respond (e.g., by pressing a mechanical button or by tapping a button on a smartphone screen or any other indication means as disclosed) when the electrotactile stimulation is felt. If the user does not press the button at a given level $X_n$ within a time window, this is taken to mean that the sensation threshold, X*, is likely to be greater than $X_n$ (i.e. $Z_n(X_n)=+1$). Otherwise, if the user presses the button, X* is too high and $Z_n(X_n)=-1$. The time window for indication can be fixed, varied by the user's profile (e.g., demographic and clinical characteristics or other factors such as prior experience with TENS devices), test current intensity, prior response time by the user, etc.

Figure 9:
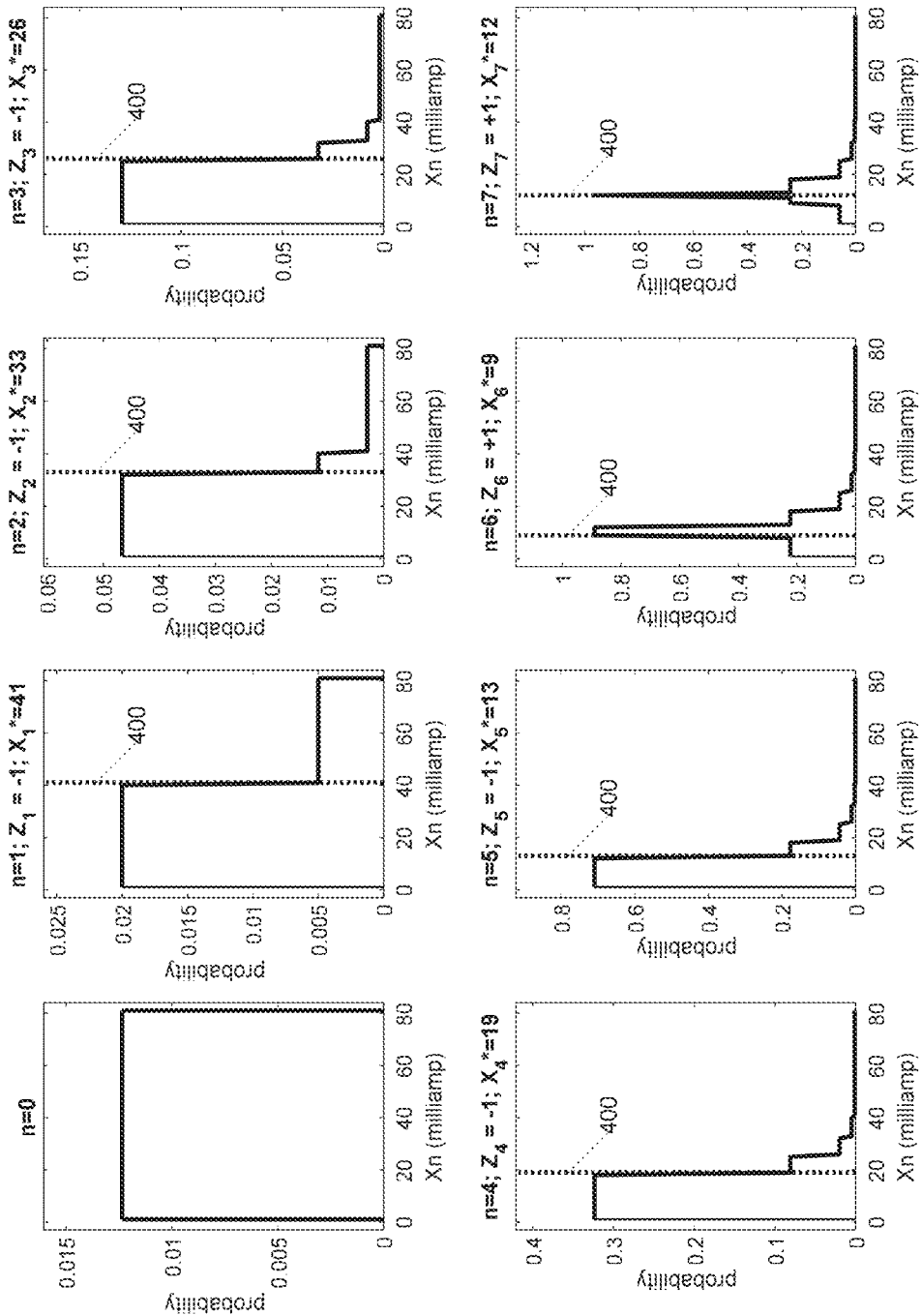
FIG. 9 is a schematic view showing a sample progression (from left to right, top to bottom) of the sensation threshold profile (probability density function) updates.
Figure 10:
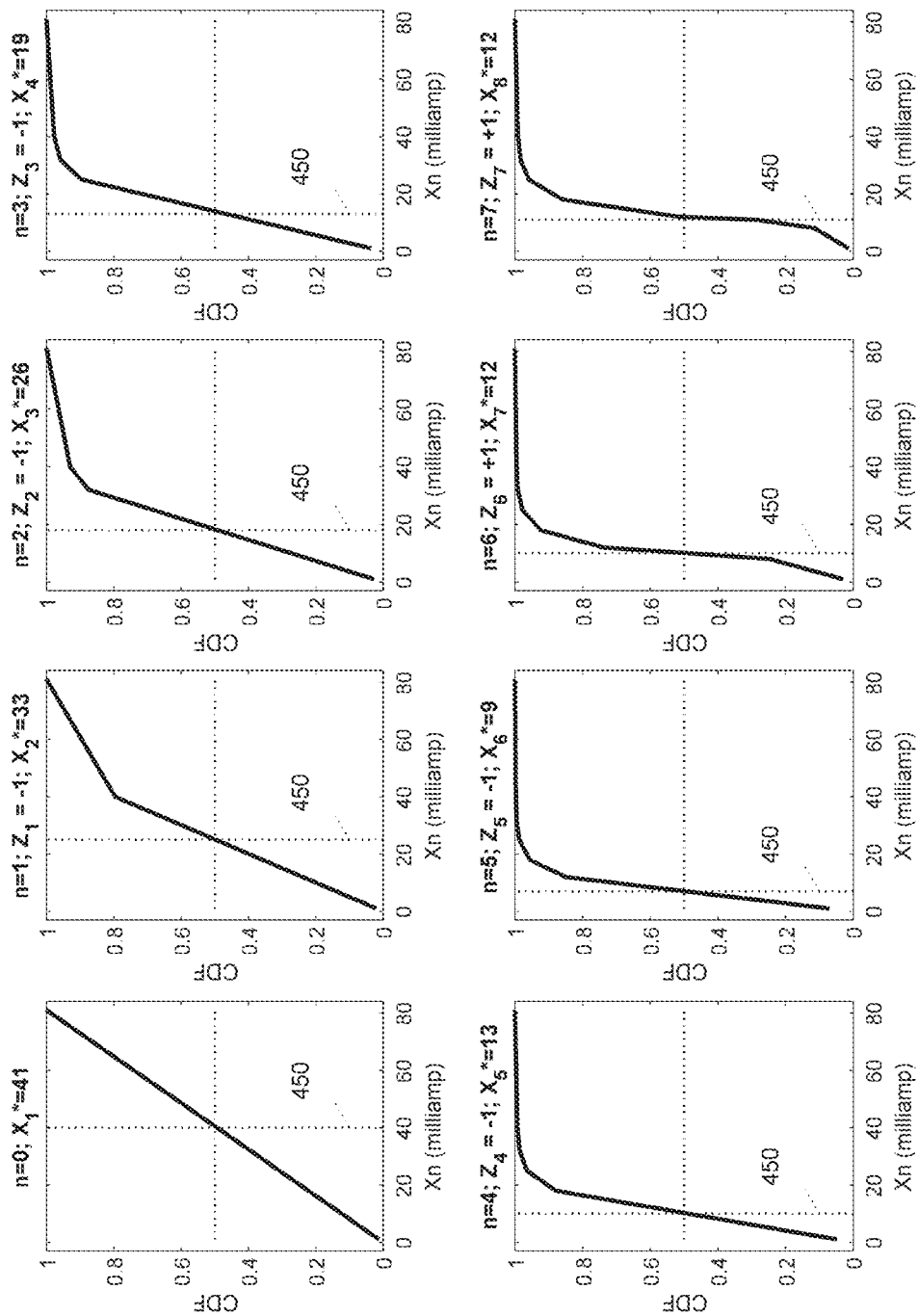
FIG. 10 is a schematic view showing the progression of the cumulative distribution functions corresponding to those sensation threshold profile updates shown in FIG. 9.

After each iteration at $X_n=x$, the posterior density function $f_{n+1}$ is updated according to Equation 1, which is essentially an application of Bayes' rule:

$$\text{if } Z_n(x) = +1 \text{ then } f_{n+1}(y) = \begin{cases} \dfrac{(1-p) \cdot f_n(y)}{\gamma(x)}, & \text{if } y < x \\ \dfrac{p \cdot f_n(y)}{\gamma(x)}, & \text{if } y \geq x \end{cases} \quad \text{(Eq. 1)}$$

$$\text{if } Z_n(x) = +1 \text{ then } f_{n+1}(y) = \begin{cases} \dfrac{p \cdot f_n(y)}{(1-\gamma(x))}, & \text{if } y < x \\ \dfrac{(1-p) \cdot f_n(y)}{(1-\gamma(x))}, & \text{if } y \geq x \end{cases}$$

where $\gamma(x) = (1 - F_n(x)) \cdot p + F_n(x) \cdot (1-p)$ and $F_n$ denotes the CDF of $f_n$ FIG. 9 shows that it amounts to weighting each side of the PDF around X* according to $Z_n$. For $Z_n=+1$, the PDF is up-weighted to the right of the line 400, down-weighted to the left of the line 400. For $Z_n=-1$, the PDF is up-weighted to the left of the line 400, down-weighted to the right of the line 400. As n increases, the PDF tends toward a singular value. $X^*_{n+1}$ is taken as the median of the cumulative density function (CDF). FIG. 10 shows the update process in CDF space. Median values of each CDF is labelled as 450.

Unlike the ramping method previously disclosed in the aforementioned U.S. patent application Ser. No. 13/678,221, issued as U.S. Pat. No. 8,948,876 (and which is incorporated herein by reference), which presents the user with a gradually increasing stimulation intensity until the user indicates that the sensation threshold (ST) has been reached, a classical PBA method moves freely above and below the midpoint of the CDF. Although this represents a potential means of reducing a user's tendency to overestimate their ST, it may also lead to queries significantly above the user's pain threshold, which results in the user being subjected to pain during the calibration process (i.e., the process to determine the user's ST). Conversely, queries which are significantly below the user's ST add to the calibration time, which is also undesirable. To overcome these limitations, another embodiment is proposed as follows:

For n=0:
  ramp the stimulation current as before, increase by 5% every 1.0 seconds, bounded such that 0.5 mA<=$I_A$<=2.0 mA ($I_A$ denotes the incremental amount of stimulation current), until either: user activates button ($Z_n=-1$), or X* is reached ($Z_n=+1$).

For iteration n+1:
  a) if the test current should decrease, this step is taken immediately without ramping, and held for up to 10 seconds waiting for the user to press the button if sensation is detected; or
  b) if the test current should increase, the algorithm must decide whether the increase is safe to take in one step or whether to ramp up the stimulation current to the test threshold—this involves prior knowledge of pain threshold data and also suggests a conservative approach, inasmuch as a slightly lengthened calibration process is greatly preferable to causing pain to the user.

Figure 11:
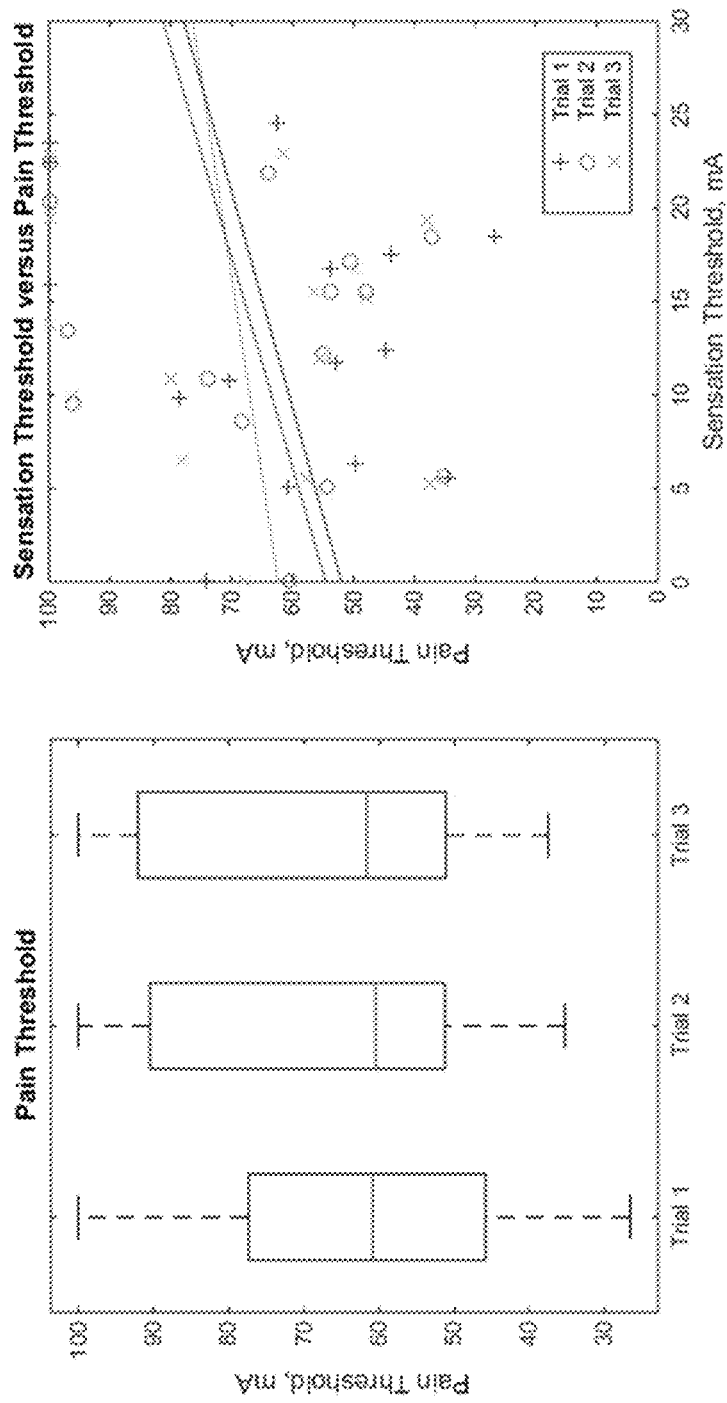
FIG. 11 is a schematic view of the pain threshold distribution of three different trials in a pain threshold experiment and the relationship between the pain threshold and the sensation threshold of the same experiment.

Based on data from a study of 15 subjects, there does not seem to be a strong correlation between pain threshold and sensation threshold (ST), though this could be explained by the subjectivity of pain. FIG. 11 shows the results of this study of 15 subjects, indicating that the median pain threshold is consistently around 60 mA, with a minimum of 26.6 mA. In all cases, the ratio of pain current to sensation current is at least 2.

Based on the above, this generation of the algorithm uses a ramp for subsequent iterations of test current if and only if:

1) the proposed test current is >2× the user's previous button press (in the absence of noise, this only happens for a small number of users, but can occur in the case of highly random selections); or
2) The proposed test current is above 20 mA.

As it will be disclosed below, the sensation threshold intensity (the first intensity to evoke electrotactile sensation) and the therapeutic intensity (the strong yet not painful stimulation) can be predicted based on user profile (e.g., demographic and clinical characteristics). In another embodiment, intensity levels of test current stimulation for a user is constructed based on predicted ranges of sensation threshold intensity and therapeutic intensity. As an example, the first test current intensity is set to 75% of the sensation threshold intensity predicted for the user if the user provides his user profile information. The first test current intensity is set to 50% of the population mean if the user fails to provide his user profile information. In subsequent presentation of test current, the intensity $IL(k+1)$ shall be two times of the previously presented test current intensity $IL(k)$ if the user indicates that the previously presented current intensity cannot be felt: $IL(k+1)=2*IL(k)$. However, the intensity level (i.e., two times the previously presented test current intensity) is modified (i.e., reduced) if such an intensity exceeds a scaled version predicted therapeutic intensity PTI (e.g., 1.25 times of the therapeutic intensity) for this user based on his user profile or such an intensity exceeds predicted pain threshold based on his user profile or an pre-set safety threshold. In one embodiment of $IL(k+1)$ modification, the test current intensity is reduced by 10%: $IL(k+1)=0.9*2*IL(k)$. In another embodiment of $IL(k+1)$ modification, the test current intensity is reduced to 110% of the predicted therapeutic intensity: $IL(k+1)=1.1*PTI$.

Choice of Starting Distribution

Figure 12:
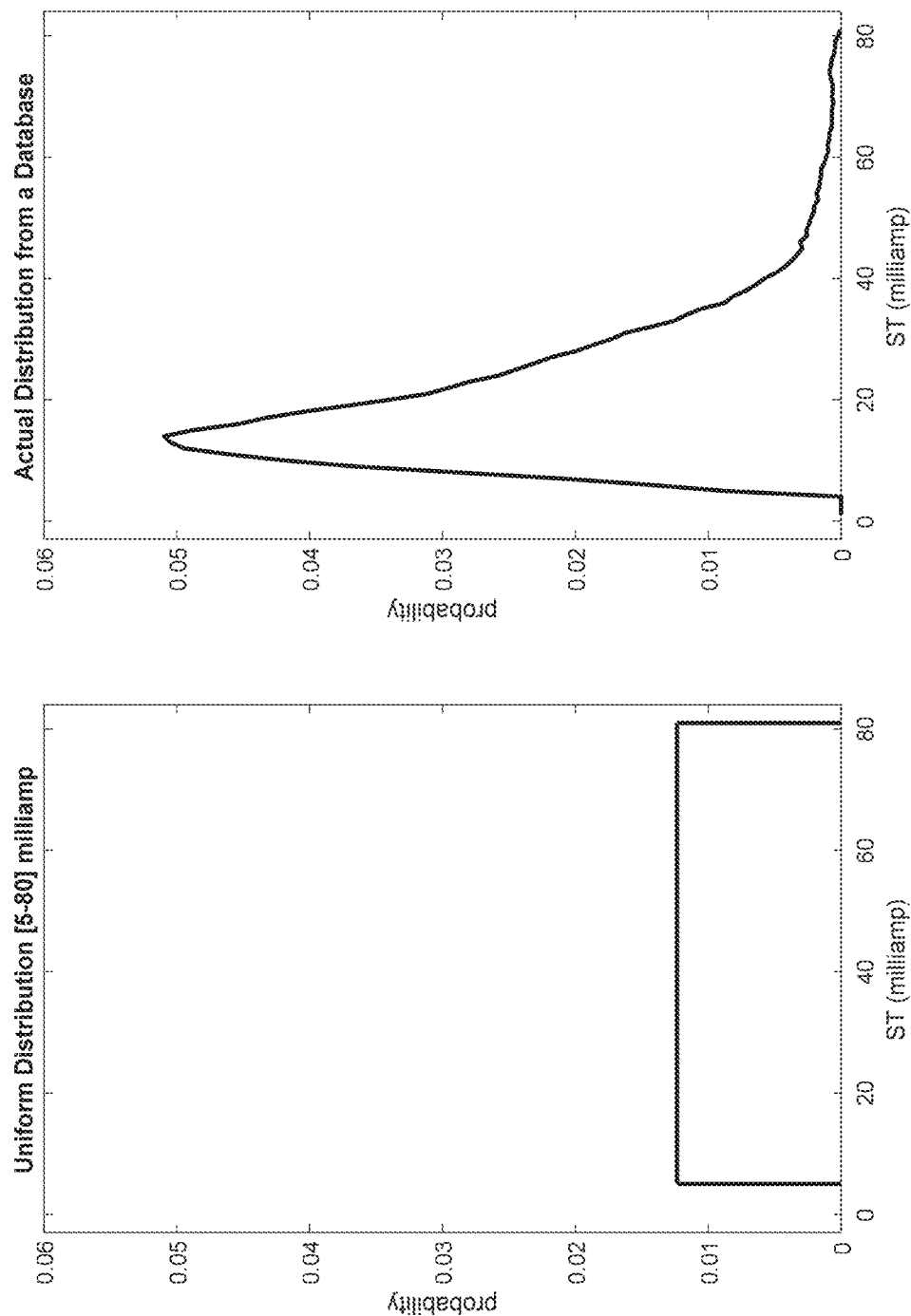
FIG. 12 is a schematic view of two possible starting points of the sensation threshold profile.

Generally speaking, PBA algorithms begin with a uniform distribution of values, as it is assumed that all numbers are equally likely in the space prior to beginning the search. In the context of sensation threshold calibration, this implies that all valid stimulation intensity levels are equally likely to be the sensation threshold for TENS user population. However, this may not be the case with the sensation threshold (ST), and further, this distribution (likelihood function) can be estimated from existing data. FIG. 12 shows the two options for the probability distributions for sensation threshold (ST). The advantages to using the actual experimental data-based probability distribution for ST include:
1) the lower center of mass in the CDF means a lower starting ramp value, lessening the chance of overstimulating;
2) the calibration for users in typical ranges is likely to reach convergence faster; and
3) unusual values in the higher end will receive greater scrutiny by the algorithm In terms of how the starting probability distribution for ST affects the query progression, FIG. 13 shows a comparison of 6 simulated measurements with each distribution. The left-most point is the first query for each distribution, i.e. the midpoint of the CDF. The point where each simulated calibration departs from the line represents the first time that the user detected sensation and pressed the button. Note that for the uniform probability distribution (the left-hand graph in FIG. 13), more queries are generally required at low values of ST, which is undesirable, as the bulk of users calibrate in this range. For the actual experimental data-based probability distribution (the right-hand graph in FIG. 13), convergence is generally achieved in fewer queries at low values, though higher ST values may take more queries to reach. Note that the query index is not a strict measure of time, as more time is required for both ramping queries and queries where the user does not "hit the button" (i.e., indicate that a sensation threshold has been reached).

Finally, it should also be noted that these two probability distributions are not the only possibilities. In an enhanced calibration where user demographics are available, information entered could be used to select a priori from a set of known distributions (i.e., a distribution for diabetics, a distribution for fibromyalgia sufferers, etc.). While the algorithm is able to converge in most cases regardless of the starting distribution, this could be a means to shorten the length of calibration and make it as brief as possible.

A prior distribution function for sensation threshold (ST) can be constructed based on various data sources or a combination of data sources. One source is a controlled study designed for collecting sensation threshold data from volunteer subjects. Data can also be from a registered database where current TENS device users store their TENS device usage data and consent to allow usage of their de-identified data for product improvement and scientific research. Sensation threshold probability distribution functions can be constructed from these datasets for TENS users based on their age, gender, body mass index, painful health conditions, chronic pain locations, pain frequency, pain patterns, sensitivity to weather and weather changes, pain ratings (average and worst pain) and pain interference scores (interference with sleep, activity, and mood), body temperature, other demographic and health conditions, and environmental conditions such as air temperature and humidity. The above referenced factors plus others commonly known in clinical literature as factors to influence electrotactile sensation are collectively referred to as elements of a user profile. A population-based ST probability distribution or likelihood function can be further modified for each user based on elements of the user profile to create a more personalized a prior ST probability distribution to guide the query process of the PBA algorithm.

Timing and Usability Concerns

The calibration algorithm should, ideally, have the following desired properties:
1) fast convergence;
2) require no more than 10 button presses;
3) require an average of 4-5 button presses; and
4) provide a measure of quality and success/failure condition.

Apart from the distribution choice described previously, there are two parameters to be selected which affect the speed of convergence and number of button presses required: p, the likelihood of the user giving the "correct" answer; and $\max(f_n)$, the threshold for the maximum peak in the PDF at which we declare the algorithm to have converged.

Choosing p

Overestimating p leads to an overly aggressive Bayesian update according to Eq. 1. This may mean that variations in the user's decisions of when to press the button cause slower-than-expected convergence in the error. Similarly, underestimating p does not provide a robust adjustment to the PDF at each iteration, again leading to slow convergence. Both types of mis-estimation can lead to an increased error in the final calibration result.

Based on an extensive simulation study, p=0.79 gives the best tradeoff between speed and accuracy and is used in a preferred embodiment of the present invention.

In another embodiment, the p value can be dynamically determined based on the timing of the user response at each query point. For example, if the user responds with a button press as soon as stimulation with a (higher) new intensity is delivered, it can be interpreted that the user is fairly certain with his response. Thus a higher p value can be used to update the PDF. On the other hand, if the user responds with a longer delay after stimulation (but still within the prescribed time period), a lower p value may be used to update the PDF.

In another embodiment, response time is compared with a relative response time. Instead of comparing a user's response time to an absolute response time reference as described above, his response time is compared with a typical response time of other users. If the user responds with a time shorter than the typical time, it can be interpreted that the user is fairly certain with his response and a higher p value can be used to update the PDF. Similarly, if the user's response time is longer than the typical time (but still within the prescribed time period), a lower p value is used to update the PDF. A typical response time reference for a different stimulation intensity can be compiled based on all available TENS users, or based on TENS users with a specific user profile characteristic (e.g., age, gender, baseline pain, etc.).

Failure/End Condition

As the range is taken to be a continuum, and we are trying to minimize the number of queries/button events, a decision rule is required on when the error is good enough. There are several non-convergence conditions for the algorithm to exit:
1) ST reaches a maximum of permissible ST range (e.g., 80 mA);
2) the number of user indications (e.g., button presses) exceeds a maximum (e.g., 10); or
3) the maximum calibration time is reached.

Ideally, however, the algorithm should find and compare the largest peak in the distribution to a threshold at each iteration. FIG. 9 showed how the PDF ideally becomes more singular at each iteration, and that this convergence to a single peak usually happens rapidly. For a discrete distribution, we could use entropy as a measure of uniformity. To approximate an entropy measure, we can use the height of the PDF peak, or the probability of X* being the true value, as a measure of convergence.

Figure 14:
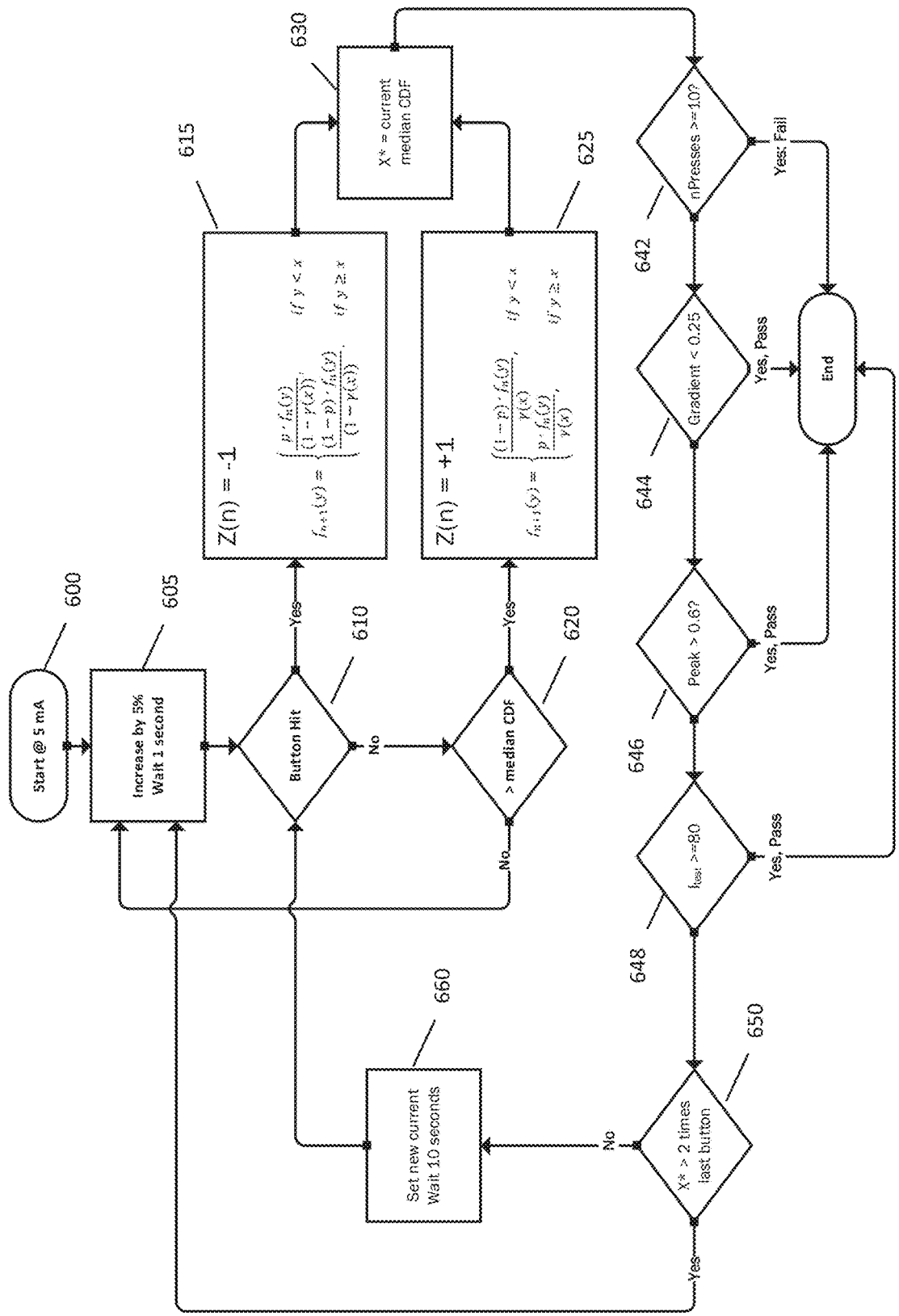
FIG. 14 is a flowchart of the steps for determining the sensation threshold intensity for a user.

FIG. 14 show a flowchart of the algorithm for determining the sensation threshold based on the probabilistic bisection algorithm. In the preferred embodiment illustrated in this figure, the initial test current is set at 5 milliamp (600, FIG. 14) and the test current intensity is increased at a rate of 5% every second (605, FIG. 14) until either an indication (via button hit) is given (610) or the median of the CFD is reached (620). If the user indicates perception of the electrotactile sensation, PDF $f_{n+1}(y)$ is updated via Z(n)=−1 (615, FIG. 14); otherwise, PDF $f_{n+1}(y)$ is updated via Z(n)=+1 (625, FIG. 14). CDF based on $f_{n+1}(y)$ is updated and its median is calculated to determine the next target test current intensity X* (630, FIG. 14). Several conditions are checked to see if the calibration process should exit: if the user has indicated ten times of perception of the electrotactile sensation before the PBA algorithm exits successfully, the algorithm shall terminate with an error due to excessive noise in user's indications (642); if the gradient, defined as the change in target test current intensity between iterations, is less than 0.25 milliamps, the PBA algorithm shall exit with a valid sensation threshold (644); if the largest peak of present PDF exceeds 0.6, the PBA algorithm shall exit with a valid sensation threshold at the peak (646); and finally if the test current intensity is greater than or equal to 80 milliamp, the PBA algorithm shall exit with a valid sensation threshold set at the maximum allowable value of 80 milliamp (648). If none of the exit conditions is met, the next target intensity X* is used as stimulation intensity to present to the user for 10 seconds for indication (660) after confirming that X* is not greater than 2 times the test current intensity in the previous iteration (650). If the target intensity X* exceeds 2 times the previous test current intensity (650), the stimulation intensity shall gradually ramp up at a rate of 5% per second to the new target value (605) and the calibration process continues until the PBA algorithm exits.

In addition to using a uniform distribution function or an actual distribution function estimated from experiment data, one could also modify the actual distribution function to improve the calibration process with a shorter calibration time. In one embodiment, the actual distribution function is broadened at its main peak region via convolution (or a low pass filter), and the probability density values are increased in the lowest regions.

In another embodiment, new exit criteria are used to reduce the number of button presses required to complete the calibration process:
1) if any peak has a height >0.6 (SUCCESS);
2) if more than one peaks is detected, but one peak is at least 2× the height of the others AND has a minimum height of 0.45 (SUCCESS);
3) if the absolute value of the current gradient (i.e., changes in stimulation intensity between iterations) is <0.25 after five or more queries (SUCCESS);
4) if the query current reaches 80 mA (GUARDED SUCCESS); or
5) if the number of button presses reaches 10 before any of the previous conditions are met (FAILURE).

While a uniform distribution function and a numerical probability density function based on actual user data are considered for the sensation threshold distribution, other probability density functions such as Poisson distribution and Gamma distribution are also considered.

Alternative Means to Provide Indication

When a user detects a target sensation from an electrical stimulation from a TENS device, the user needs to indicate such sensation so that the sensation can be registered for later use. Such an indication can be manual or automated, it can also be done voluntary or involuntarily, subjectively or objectively.

In one preferred embodiment, the indication is done by pushing a button on a physical device (e.g., on TENS device 100 or a smartphone 180 running an appropriate App, etc.). In another embodiment, the indication is accomplished by one or more gestures to a physical device that can detect gestures, such as those with an embedded accelerometer (e.g., carried by TENS device 100 or a smartphone 180 running an appropriate App). The physical device can be with a button or without any mechanical actuator (button), and it can be directly or remotely connected to the stimulation apparatus. In yet another embodiment, the indication is done by tapping the screen or a button on a touch screen of a device (e.g., a smartphone), and the device can be directly or remotely connected to the stimulation apparatus.

The indication can also be detected automatically. When electrical stimulation causes the peripheral sensory nerve to be activated, such sensory activation will result in local or central anatomical responses. Blood flow may increase locally, which can be detected via galvanic skin response sensors or temperature sensors. Local muscle actions may be triggered, particularly for electrotactile pain threshold sensations and electrotactile tolerance threshold sensations. Therefore, an EMG sensor or an electromechanical sensor such as accelerometer can be used to detect local muscle actions and to register the indication automatically. The electromyography (EMG) sensor, a part of electrophysiology sensor 139 (FIG. 7), can detect electrical activities of muscle fibers. An accelerometer can detect mechanical movement of muscle contraction.

The indication can also be detected involuntarily through other sensors. Somatosensory evoked potential (a brain neuron cell response to sensory stimulation) can be detected and measured via electroencephalogram (EEG) electrodes and associated bio-amplifier circuitry 151 (FIG. 7) placed on the head of the user. A video recorder or a camera can also be used to measure the size of the user's pupils to register the indication. Registration of the indication is done by detecting changes of pupil size that synchronizes with (but does not have to coincide with) the onset of the electrical stimulation, particularly stimulation with a new (higher) intensity. The front camera on a smartphone 180 can be used to measure pupil size to detect any changes. Onset of the electrical stimulation could also serve as a trigger signal for the camera to operate in a designated mode to detect pupil size change by adjusting zoom, brightness, and/or other factors to improve the detection outcome.

Presentation of Stimulation Sequence During Calibration

The calibration process disclosed in U.S. patent application Ser. No. 13/678,221, issued as U.S. Pat. No. 8,948,876 (and which is incorporated herein by reference), presents TENS users with stimulation pulses whose amplitude gradually increase with time while other factors (such as pulse duration and frequency) are fixed. This is necessary as the search is a single threshold detection process (i.e., the transition from non-detectable stimulation to detectable stimulation). The present invention discloses an apparatus and method that presents discrete stimulation pulse patterns in order to construct a collection of indications (sensed or not sensed) with respect to the stimulation intensity of the pulse patterns. As a result, one or more parameters of the stimulation pulses can be modified at the same time.

In one preferred embodiment, if the first pulse pattern (with A1 and D1 as the amplitude and duration of the pulses) received a negative indication (no sensation) from the user, both pulse amplitude and duration can be increased for the second pulse pattern (with A2>A1 and D2>D1). If user indication is positive, the third pulse with A1 and D2 will be presented to the user first for his indication if such a combination will consume less battery power than the combination of A2 and D1. Of course, if the third pulse cannot be sensed by the user, the fourth pulse (with A2 and D1) will be presented to the user for indication. The above example illustrates the advantage of discrete pulse pattern presentation in the context of battery power consumption, an important consideration in any portable/wearable device use.

In one preferred embodiment, the determination of which parameter serves as the primary factor to adjust depends upon one or more characteristics of the user. As an example, for a user with age 40 or younger, pulse frequency can be increased to a maximum value first before pulse amplitude is increased when constructing a stimulation pulse pattern with increased intensity. For users with a specific pain condition (e.g., fibromyalgia), pulse duration is preferentially increased before pulse amplitude and frequency.

Indication of Other Electrotactile Sensation Levels

In the foregoing description, electrotactile sensation threshold is the target sensation for the calibration process. However, other electrotactile sensation levels, such as electrotactile pain threshold, "strong yet not painful" level, and electrotactile tolerance threshold, may be the target sensation for the calibration process. Electrotactile sensation threshold is the lowest stimulation intensity and is generally a well understood concept. Therefore, it is a preferred target in the initial calibration process. However, there are cases when other calibration targets may be needed and the same search process can be used to determine the stimulation pulse intensity that evokes the target sensation.

In one preferred embodiment, a user may request a calibration to "strong yet not painful" sensation after the user has used TENS therapy with a specific pulse pattern (Pattern A) for some time due to nerve habituation (i.e., where the user's nervous system becomes desensitized to a stimulation pattern after repeated exposure to such a stimulation pattern). While increasing pulse amplitude is the most straightforward way to overcome nerve habituation, it may not be most desirable due to energy consumption and further nerve habituation effect. Since the user is familiar with the "strong yet not painful" sensation, calibration can be done directly towards this sensation target but utilizing different stimulation patterns. The calibration process can present a sequence of stimulation patterns with a lower pulse amplitude but with increased pulse duration or increased pulse frequency or altered pulse morphology, or a combination thereof. Once the user identifies the pulse pattern (Pattern B) that gives the same "strong yet not painful" sensation, the pulse pattern will be used for subsequent therapy sessions. After a pre-determined period (e.g., two weeks), the stimulation pulse pattern will revert to Pattern A so that the user does not develop nerve habituation towards Pattern B. Identification and alternating among more than two pulse patterns may also be used.

In another preferred embodiment, alternative pulse patterns that evoke "strong but not painful" sensation are identified not for the purpose of overcoming nerve habituation but for battery power conservation purpose. After identifying the first pulse pattern (with pulse duration D1 and amplitude A1) that evokes "strong but not painful" sensation, the user may request a second calibration if the battery consumption of such a pulse pattern is not optimal. Alternative pulse patterns, such as pulses with longer duration (D2>D1 and D3>D1) but lower amplitude (A2<A1, A3<A1) will be presented to the user. If the user confirms the new pulse pattern (D3 and A3) gives the same sensation as the first pulse pattern (D1 and A1), therapeutic sessions with the new pulse pattern (D3 and A3) will be used to extend battery life between recharges.

In another preferred embodiment, alternative pulse patterns that evoke "strong but not painful" sensation are identified for the purpose of increased comfort during therapy use at night. Two or more pulse patterns can be calibrated to yield the same "strong but not painful" sensation during the day for a user. Overnight therapies with one of identified pulse patterns per night will be delivered, and the sleep quality is used as the tie-breaker selection criterion to determine which pulse pattern is optimal for the user to use at night. We note that in this preferred embodiment, the search criteria are objective measurements of sleep quality (e.g., total sleep time, sleep efficiency, and period leg movement index) instead of subjective perception criteria.

In another preferred embodiment, alternative pulse patterns that evoke "strong but not painful" sensation are identified for the purpose of long-term use comfort for users with certain painful conditions. For example, if most users with fibromyalgia pain prefer therapies with pulse patterns having a lower pulse frequency, then a new fibromyalgia user shall be presented with several stimulation patterns with different pulse frequencies. The user shall then identify one or more pulse patterns that produce a similar "strong but not painful" sensation and the same short-term comfort level. The TENS device shall select the pattern with the lowest pulse frequency for long-term comfort even before the user with fibromyalgia experiences any long-term discomfort resulting from higher pulse frequency stimulation.

Validation of Sensation Threshold

While electro-tactile sensation threshold may not be predicted precisely for a TENS user, a range can be specified with high confidence based on the clinical and demographic characteristics of the user. User characteristics may include age, gender, height, weight, body mass index, health conditions (e.g., presence or absence of diabetes, fibromyalgia, previous back injury, etc.), pain locations (e.g., feet/ankle, lower back, arms, hand/wrist, head, etc.), pain duration, pain patterns (e.g., in the morning, all the time, when resting, etc.), pain frequency (e.g., every day, several times a week, rarely, etc.), feeling about pain or pain catastrophizing (e.g., degree of feeling towards statements like "when I am in pain, I become afraid that the pain will get worse", etc.), weather sensitivity (e.g., rain will worsen the pain, high humidity will worsen the pain, etc.), pain ratings (e.g., pain intensity, pain interference with sleep, activity, and mood, etc.), etc.

Based on sensation threshold data collected from a large number of TENS users, a predictive model is created to estimate the expected sensation threshold range based on TENS users' clinical and demographic characteristics. In a preferred embodiment, the target sensation threshold (TST) model is given as follows:

$$TST1=16.78+0.14*[Age]+0.09*[Weight]+2.80*[Diabetes]+0.89*[Spinal\_Stenosis]+0.78*[Chronic\_Regional\_Pain]+0.46*[Leg\ or\ Foot\_Injury]+0.31*[Other\ Med\ Hist]+0.32*[PainDuration\ OneToThree\_Years]+0.80*[Hot\_Weather]-4.18*[Female]-0.08*[Height]-0.22*[BMI]-0.61*[Herniated\_Disc]-1.69*[Shingles]-0.69*[Humid\_Weather]$$

If a user has diabetes, variable [Diabetes] is set to 1. Otherwise it is set to 0. Similarly, if the user is sensitive to humid weather condition (i.e., pain is greater when the humidity is high), variable [Humid_Weather] is set to 1.

Depending upon the number and types of characteristics provided by the TENS user, different predictive models are developed to resolve ambiguity of missing information. In a preferred embodiment, the TST model for TENS users providing only age (in years), gender, and whether they have diabetes or not, is given as follows:

$$TST2=6.16+0.14*[Age]-4.36*[Female]+2.93*[Diabetes]$$

In a preferred embodiment, the sensation threshold range is constructed using a target value and a range interval. The target value is given as above. The range for TST2 is defined as $10^{th}$ to $90^{th}$ percentile of TST2 values observed from a dataset of 6376 TENS users:

$$\text{Expected Range for } TST2=[0.514*TST2, 1.627*TST2].$$

As an example, for a female TENS user of 60 year old with diabetes, her target sensation threshold is 13.13 milliamp and expected range of the target sensation threshold is between 6.75 milliamp and 21.36 milliamp. Therefore, the set of expected values of the target sensation threshold for this user is all intensity values between 6.75 milliamp and 21.36 milliamp.

The range interval depends upon the amount and type of clinical and demographic characteristics provided by the user. For example, age is found to be a reliable predictor of the sensation threshold, and missing age information will cause the range interval to increase.

In a preferred embodiment, the TENS user enters his/her demographic and clinical characteristic information via the App running on smartphone 180. Prior to first therapeutic use, the TENS user is asked to set up therapeutic intensity by indicating his/her electro-tactile sensation threshold via a pre-defined indication method. The indication method can be a gesture to a physical device remoted connected to the stimulator (e.g., smartphone 180) or an interaction with a mechanical actuator located on the housing of the stimulator. Determination of the electrotactile sensation threshold can be accomplished by utilizing calibration methods such as the probabilistic binary search approach or the gradual intensity ramp up approach. The predictive model calculates the expected sensation threshold range based on information provided by the user. The user-indicated sensation threshold is compared with the expected range. If the sensation threshold falls within the range, the sensation threshold is considered to be accurate and is used by a subsequent prediction model to determine the therapeutic stimulation intensity. If the sensation threshold falls outside the range, a feedback message is given to the user via the App to request another calibration. Other means of feedback include a vibration pattern from the TENS device. The feedback message can be optionally customized to offer targeted hints to the user. For example, if the indicated sensation threshold is below the lower bound of the expected range, the user is prompted to delay the calibration process until the cold sensation of the electrode gel pads disappears (i.e., when the temperature of the electrode gel reaches an equilibrium with the skin temperature). If the indicated sensation threshold is above the upper bound of the expected range, the user is reminded to indicate the first sensation of electrical stimulation, not the preferred sensation for therapeutic stimulation intensity that the user may have previously experienced.

In another embodiment, the indicated sensation threshold (from either a first-time calibration or a subsequent recalibration) is compared with the expected range so that a confidence level (CL) or accuracy is assigned to the sensation threshold. The confidence level is high if the sensation threshold is near the center of the range and low if the sensation threshold is near the edge of the range or outside the range. In the example above, an indicated sensation threshold of 15 milliamp by the female TENS user will be given a high confidence level (e.g., CL=100%) while an indicated sensation threshold of 20 milliamp by the same user will be given a low confidence level (e.g., CL=15%). The confidence level is used in the subsequent prediction model in addition to the value of the sensation threshold. As an example, both sensation threshold level and user profile characteristics contribute to the prediction of the therapeutic stimulation intensity. If the confidence level of the sensation threshold is low, its contribution towards the therapeutic intensity prediction is deemphasized while the user profile elements are emphasized. In the example above, the indicated sensation threshold of 15 milliamp will contribute more towards prediction of the therapeutic intensity prediction than an indicated sensation threshold of 20 milliamp.

In yet another embodiment, a different stimulation pattern (e.g., short pulse width or long pulse width) is selected and presented to TENS users with a specific clinical condition (e.g., with fibromyalgia or with diabetes), or with a combination of clinical conditions, and the sensation threshold is recorded. The sensation threshold is then used in the subsequent prediction model to determine therapeutic stimulation intensity for the selected stimulation pattern for the TENS user with specified clinical conditions.

In yet another embodiment, more than one stimulation pattern (e.g., burst and regular) of stimulation pulses are presented to TENS users with a specific clinical condition (e.g., with prior back injury) and sensation threshold results are recorded for each stimulation pattern. In one embodiment, the stimulation pattern with a lower sensation threshold may be used as the preferred stimulation pattern for a given TENS user and the sensation threshold and stimulation pattern are passed to the prediction model. In yet another embodiment, all sensation thresholds are then used in the subsequent prediction model to determine a preferred stimulation pattern and the associated therapeutic stimulation intensity.

Prediction of Therapeutic Intensity

Although there is a strong correlation between sensation threshold and therapeutic stimulation intensity, it is possible and desirable to enhance the prediction accuracy of the therapeutic stimulation intensity by considering a user's clinical and demographic characteristics in addition to the sensation threshold. In a preferred embodiment, a user-indicated sensation threshold (uiST) that is within the expected sensation threshold range is used to predict therapeutic intensity (TI) together with demographic and clinical characteristics of the user. One such prediction model is given below:

$$TI1=8.74+0.06*[Age]-2.61*[Female]+1.06*[uiST]$$

In another embodiment, the user-indicated sensation threshold is not used to predict the therapeutic intensity if the indicated sensation threshold is outside the expected sensation threshold for that user. One such prediction model is given below:

$$TI2=17.93+0.24*[Age]-8.18*[Female]+5.33*[Diabetes]$$

In yet another embodiment, the user-indicated sensation threshold is used in a prediction model together with the confidence level (CL) associated with the sensation threshold. As an example, a prediction model that combines TI1 and TI2 based on CL can be constructed as follows:

$$TI=CL*TI1+(1-CL)*TI2$$

In another embodiment, therapeutic intensity is predicted based on a user's demographic and clinical characteristics without any consideration of the sensation threshold indicated by the user. In yet another embodiment, therapeutic intensity is predicted exclusively based on the indicated sensation threshold.

Patterns of sensation threshold values (in response to multiple stimulation patterns) can also be used to select the stimulation pattern in addition to predicting the therapeutic intensity associated with the selected stimulation pattern. For example, if sensation threshold values are similar (say within 10% of each other) for both short and long duration stimulation pulses, a short duration pulse pattern will be selected and the therapeutic intensity for the selected pattern will be predicted. In another embodiment, the short duration pulse pattern is preferred only when the TENS user possesses certain demographic and/or clinical characteristics (e.g., female with fibromyalgia).

In addition to demographic and clinical characteristics, a TENS user may provide his/her preferred goal for managing chronic pain. For example, if a user emphasizes better sleep as a priority goal, a regular pulse pattern with a lower therapeutic intensity but more frequent sessions can be set for the user.

Therapeutic intensity prediction can also be modified based on contemporary changes experienced by TENS users. As a user receives TENS therapy with the therapeutic stimulation pattern and intensity predicted based on baseline demographic and clinical characteristics, the user may experience changes in pain conditions as measured either subjectively through pain ratings on the App (running on smartphone 180) or objectively through sleep and activity tracking by the TENS device 100. Therapeutic stimulation intensity and pattern can thus be adjusted based on a TENS therapy outcome. For example, if the pain ratings decrease after two weeks of TENS therapy, the therapeutic intensity prediction model can incorporate such a positive trending into its prediction outcome so that the therapeutic intensity for week three is reduced. During the third week with a reduced therapeutic intensity, if the pain ratings hold steady, the same intensity is predicted for subsequent weeks. If the pain ratings increase, previous higher therapeutic intensity is predicted for subsequent weeks. Similarly, if better sleep is an important goal as indicated by the user and sleep tracking results show little progress in sleep quality improvement during the first two weeks of TENS therapy, a higher evening therapeutic intensity is predicted to increase the TENS therapy dosage before bedtime.

Other quantifiable conditions considered include electrode gel material, strap composition and construction, TENS device dimensions, location of TENS device placement, etc. Changes in these conditions may have an impact on how electrical pulses are felt by TENS users. For example, electrode gels with less moisture content may cause electrode-skin contact to be less uniform and results in a slightly more robust sensation of the same electrical stimulation. In one embodiment, electrode gel composition is included in the prediction model. When an electrode with a gel composition different from that used for sensation threshold measurement is used for therapy, the therapeutic intensity model will adjust the intensity accordingly to take into consideration the effect of the gel composition change.

Health Cloud Database Management

A "health cloud database" refers to any data resource where data from more than one TENS user are stored and can be shared with one or more TENS devices. A health cloud database allows one user to benefit from the experience of other users using the same or similar therapeutic device or modality.

In one preferred embodiment, TENS users share their anonymous data on the health cloud database. Shared data include their demographic and clinical information such as age, gender, weight, health conditions related to chronic pain, pain locations, pain duration, and pain frequency (daily versus several times a week). Users also share their TENS therapy utilization data such as daily therapy sessions, initial therapeutic intensity setup (in relation to their electrotactile sensation threshold), subsequent therapeutic intensity adjustments over time, and time course of TENS therapy use. Shared data may also include subjective feedback of pain intensity and pain interference with sleep, activity, and mood prior to and throughout a TENS therapy use period; objective tracking of health dimensions such as activity level (steps taken), gait patterns, sleep duration, sleep quality, periodic leg movement count over time; and changes in medication intake.

When a user with a TENS therapy duration exceeding a pre-defined threshold (e.g., 60 days) is added to the health cloud database, prediction models are updated based on a new dataset. In one preferred embodiment, the new dataset is the existing dataset plus the newly added user. In another embodiment, the new dataset is the same size as the existing dataset by replacing data from one user in the existing dataset with the data from the newly added user if the newly added user has a better therapeutic outcome (e.g., if sleep quality improvement is more evident). In one preferred embodiment, data (from multiple users) in a dataset for creating prediction models contribute to the models equally. In another embodiment, each user in the dataset will contribute differently with a different weight for each user based on certain criteria. Incorporating each data point using a different weight can be achieved using weighted least square regression. Weight (the level of contribution to prediction models) of each user can be based on effectiveness of the therapy (e.g., a reduction in pain intensity levels between day 60 and day zero of using TENS therapy) in one preferred embodiment. Weight can be based on an objective measure of outcome such as sleep duration changes between week 10 and week one in another embodiment. Weight can also be based on frequency at which therapies were performed by each user.

In one preferred embodiment, the prediction model calculates the initial therapeutic intensity level based on sensation threshold and demographic and clinical characteristics. In another embodiment, the prediction model calculates the therapeutic intensity level adjustment over time based on an initial therapeutic intensity level and the objective tracking of health conditions (e.g., sleep duration and sleep quality measures). In yet another embodiment, the prediction model calculates recommended therapy session count (i.e., the number of therapy sessions occurring during a given time interval) based on sensation threshold, demographic and clinical characteristics, and goal setting priorities (e.g., reducing pain interference with sleep is the top priority). In yet another embodiment, the prediction model calculates recommended therapy session count distribution between daytime use and nighttime use based on sensation threshold, demographic and clinical characteristics, and goal setting priorities (e.g., reducing pain interference with sleep is the top priority).

In one preferred embodiment, a new user is matched with a group of existing users on the health cloud database. "Match" means similar demographic and clinical characteristics such as having the same gender and age difference within 5 years. "Match" could mean pain locations overlap between the new user and the selected group of existing users. "Match" could also mean the new user shares the same goal of "sleep better" with the selected group of existing users. Instead of using the prediction model created based on all available users in the health cloud database, a prediction model created based on only those "matching" users will be used for the new user.

Data from users with unfavorable therapy outcomes can also be used to guide new users to improve their therapeutic outcome. Unfavorable outcomes may be those with no improvement in pain after a fixed period of use (e.g., 60 days). Unfavorable outcomes may also include those who stopped TENS therapy use shortly after first use. In one preferred embodiment, initial therapeutic intensity levels as a function of their indicated sensation threshold and demographic/clinical characteristics is modeled. In another embodiment, therapy session patterns (i.e., how many therapy sessions occur per day within a period of first use) are compiled. In yet another embodiment, therapy session distributions (daytime use versus nighttime use) as a function of therapy goals (e.g., to improve sleep) are calculated.

Because of inter-user variability, a TENS user is not expected to follow the recommendations of prediction models precisely. When the TENS user adjusts therapeutic intensity level or selects a different therapy schedule, their therapeutic setup and usage pattern can be monitored and compared with that of users with unfavorable therapeutic outcome. If a close match is found (by taking into consideration factors such as demographic/clinical characteristics, therapy goal, and other factors (like medication intake, prior experience with pain therapies, etc.), an alert can be issued to the user or their caregivers for possible corrective actions as they are more likely to gain no pain-relieving benefits by continuing the current practice.

Modifications of the Preferred Embodiments

It will be appreciated that the present invention provides a transcutaneous electrical nerve stimulator with a means for determining the proper therapeutic stimulation intensity by an efficient and reliable method to estimate the sensation threshold using a probabilistic model.

When a sensation threshold is determined, a likelihood of accuracy can be estimated. A low likelihood of accuracy will trigger a feedback to the user to suggest a re-calibration. If a user agrees to recalibrate, the same Probabilistic Bisection Algorithm (PBA) is used in one preferred embodiment. In another embodiment, a different calibration procedure other than the Probabilistic Bisection Algorithm (PBA) is used. Instead of presenting stimulation pulses with discrete and disjoint intensity levels as in PBA, stimulation pulses with continuously increasing intensity levels are presented to the TENS user until the user indicates a sensation is felt. In another embodiment, stimulation patterns with gradually increasing intensity levels are presented to the user to determine the sensation threshold during the first calibration round. If the user fails to indicate a sensation threshold with an acceptable likelihood of accuracy, the PBA method is used in a second calibration round.

To determine the likelihood of accuracy, the sensation threshold is compared against a likelihood function. When the likelihood function $L(ST)$ value at the selected sensation threshold $ST$ is below a threshold $RC$, a re-calibration suggestion is issued to the user. The likelihood function $L(ST)$ can take a form similar to the initial PDF or a different form. The $L(ST)$ can take the same value for a range of $ST$ values (above the RC value) and a different value (below the RC value) for other ST values. The likelihood function L(ST) can take the form of a continuous function (such as Gaussian function). The likelihood function can be the same for all users or the function specifications can depend upon demographic and clinical factors such as age, gender, body mass index, number and type of painful medical conditions, location of pain, frequency of pain, and patterns of pain. Other factors such as pain sensitivity to weather conditions and pain durations are also considered. Pain ratings (average pain, worse pain) and pain interference levels (with sleep, activity, mood, etc.) are also considered. The recalibration threshold RC depends on the choice of likelihood function. Additionally, the RC (for the same likelihood function choice) may depend upon the calibration history path (see FIG. 13). In one embodiment, the RC is lower than the default value for a user if the user needed a much higher number of queries to complete the calibration process than the expected number of queries under normal conditions to reach that sensation threshold level from a known test current intensity.

Once the sensation threshold for a TENS user is estimated, therapeutic stimulation intensity is then calculated for the user. In one preferred embodiment, the therapeutic stimulation intensity is 5 dB above the sensation threshold. In another embodiment, a linear mapping of the form below is used.

[Therapeutic Intensity]=Offset+Scale*[Sensation Threshold]

In a preferred embodiment, the coefficient Scale is a constant for all users. In yet another embodiment, the coefficient Scale is a function of user's demographic and clinical factors.

In another embodiment, therapeutic stimulation intensity is estimated based on both sensation threshold and demographic and clinical factors, including baseline pain ratings. To account for the logarithmic behavior of the electrical stimulation effect, logarithmic transformation for [Therapeutic Intensity] and [Sensation Threshold] is used in another embodiment (represented by log(Therapy) and log(SenTh)):

log(Therapy)=ScaleA*log(SenTh)+Fun(BaseCovariates)+ScaleB

Fun(BaseCovariates) is a function that maps demographic, clinical, and baseline pain rating factors to an incremental value to [Therapeutic Intensity]. In one embodiment, the function is a linear function. In another embodiment, the function is a nonlinear function. In yet another embodiment, the function is a nonlinear fuzzy function.

In a preferred embodiment, datasets from all available users are used to determine the parameters and coefficients for functions, thresholds, and probabilities. In another embodiment, only users who meet certain criteria are included in the datasets. Examples of such criteria include limiting users to those who used the TENS device for a minimum number of days (for example, 8 weeks), and/or to those who experienced a minimum reduction in pain ratings over a period of time (for example, 2 or more point reduction in pain based on 11-point visual analog scale for pain over 10 week period), and/or to those who were able to reduce their intake of prescription pain medications by 25% or more, and/or to those who improved their sleep efficiency by 10%, and/or to those who experienced 15% or more improvement in patient global impression of change (PLIC).

Furthermore, it should be understood that many additional changes in the details, materials, steps and arrangements of parts, which have been herein described and illustrated in order to explain the nature of the present invention, may be made by those skilled in the art while still remaining within the principles and scopes of the invention.

What is claimed is:

1. Apparatus for determining a target stimulation intensity level of electrical stimulation to a user that evokes an immediate electrotactile sensation from the user, said apparatus comprising:
   a stimulation unit for electrically stimulating body tissue of the user;
   a control unit for determining an intensity level of a next electrical stimulation to be delivered to the user by the stimulation unit based on a likelihood function that specifies the likelihood of a range of intensity levels to be the target stimulation intensity level;
   an indication unit for the user to indicate when the immediate electrotactile sensation is felt when the stimulation unit stimulates the user at the intensity level; and
   a calculation unit for updating the likelihood function for the range of intensity levels to be the target stimulation intensity level based on input to the indication unit from the user;
   wherein the control unit is further configured to update the target stimulation intensity level based on the updated likelihood function, and either (i) establish the updated stimulation intensity level as the target stimulation intensity level for invoking the immediate electrotactile sensation from the user, or (ii) set the updated stimulation intensity level as the intensity level of the next electrical stimulation to be delivered to the user to obtain an additional indication of the immediate electrotactile sensation felt by the user.

2. Apparatus according to claim 1 wherein the immediate electrotactile sensation is the sensation threshold.

3. Apparatus according to claim 1 wherein the immediate electrotactile sensation is the pain threshold or the tolerance threshold.

4. Apparatus according to claim 1 wherein the indication is an input from the user to the indication unit within a pre-determined time window following the onset of electrical stimulation at a given intensity level.

5. Apparatus according to claim 1 wherein the likelihood function is initially set to be a uniform distribution function.

6. Apparatus according to claim 1 wherein the calculating unit updates the likelihood function by increasing likelihood values for intensity levels lower than the intensity level and decreasing likelihood values for intensity levels higher than the intensity level if the user provides an indication that the electrotactile sensation is felt when stimulation is delivered to the user at the intensity level.

7. Apparatus according to claim 1 wherein the calculating unit updates the likelihood function by increasing likelihood values for intensity levels higher than the intensity level and decreasing likelihood values for intensity levels lower than the intensity level if the user fails to provide an indication that the electrotactile sensation is felt when stimulation is delivered to the user at the intensity level.

8. Apparatus according to claim 1 wherein the likelihood function is a probability density function of the range of intensity levels to be the target stimulation intensity level.

9. Apparatus according to claim 8 wherein the intensity level of a next electrical stimulation is reset to a second threshold if the next intensity level value exceeds a first threshold.

10. Apparatus according to claim 9 wherein the first threshold is calculated based on a user profile of the user.

11. Apparatus according to claim 10 wherein the user profile includes at least one of the following: age, gender, body mass index, painful health conditions, chronic pain locations, pain frequency, pain patterns, sensitivity to weather and weather changes, pain ratings, pain interference scores, body temperature, weather conditions, and previously determined target stimulation intensity levels.

12. Apparatus according to claim 9 wherein the second threshold is set to two times of current intensity level value.

13. Apparatus according to claim 8 wherein the stimulation unit gradually ramps up stimulation intensity from the current intensity level to the next intensity level if the next intensity level value exceeds a threshold.

14. Apparatus according to claim 1 wherein determination of the updated target stimulation intensity level is based on a first property of the updated likelihood function, and further wherein the first property of the updated likelihood function is the intensity level at which the likelihood function reaches a maximum.

15. Apparatus according to claim 1 wherein the likelihood function is modified by a profile of the user through a modification function.

16. Apparatus according to claim 1 wherein the apparatus is further configured to assess the accuracy of the target stimulation intensity level, the apparatus further comprising:

a second calculation unit for calculating a set of expected target stimulation intensity levels based on a profile of the user; and an assessment unit to determine the accuracy of the target stimulation intensity level based on the relationship between the target stimulation intensity level and the set of expected target stimulation intensity levels.

17. Apparatus according to claim 1 wherein the additional indication of the immediate electrotactile sensation felt by the user is used to update the likelihood function, wherein determination of the updated target stimulation intensity level is based on a second property of the updated likelihood function.

18. Apparatus according to claim 17 wherein the second property of the updated likelihood function is that a maximum value of the updated likelihood function exceeds a threshold.

\* \* \* \* \*